United States Patent
Scolnick et al.

(10) Patent No.: US 12,144,786 B2
(45) Date of Patent: Nov. 19, 2024

(54) METHODS OF TREATMENT FOR ANOREXIA NERVOSA, BULIMIA AND RELATED CLINICAL SYNDROMES

(71) Applicant: Homeostasis Therapeutics, Limited, Bronx, NY (US)

(72) Inventors: Barbara Scolnick, Waban, MA (US); Caroline Beckwith, New York, NY (US)

(73) Assignee: Homeostasis Therapeutics LLC, Bronx, NY (US)

( * ) Notice: Subject to any disclaimer, the term of this patent is extended or adjusted under 35 U.S.C. 154(b) by 404 days.

(21) Appl. No.: 17/216,033

(22) Filed: Mar. 29, 2021

(65) Prior Publication Data
US 2021/0299065 A1  Sep. 30, 2021

Related U.S. Application Data

(60) Provisional application No. 63/000,786, filed on Mar. 27, 2020.

(51) Int. Cl.
| | |
|---|---|
| *A61K 31/135* | (2006.01) |
| *A23L 33/00* | (2016.01) |
| *A23L 33/115* | (2016.01) |
| *A23L 33/125* | (2016.01) |
| *A23L 33/17* | (2016.01) |
| *A61K 9/00* | (2006.01) |
| *A61P 3/00* | (2006.01) |
| *A61P 3/02* | (2006.01) |

(52) U.S. Cl.
CPC .......... *A61K 31/135* (2013.01); *A23L 33/115* (2016.08); *A23L 33/125* (2016.08); *A23L 33/17* (2016.08); *A23L 33/30* (2016.08); *A23L 33/40* (2016.08); *A61K 9/0019* (2013.01); *A61P 3/00* (2018.01); *A61P 3/02* (2018.01); *A23V 2002/00* (2013.01)

(58) Field of Classification Search
CPC .................................................. A61K 31/135
See application file for complete search history.

(56) References Cited

U.S. PATENT DOCUMENTS

| | | |
|---|---|---|
| 2006/0135608 A1 | 6/2006 | Horrobin et al. |
| 2016/0175378 A1 | 6/2016 | Bistrain et al. |
| 2017/0296501 A1 | 10/2017 | Lowery et al. |
| 2018/0177745 A1 | 6/2018 | Hashimoto |

OTHER PUBLICATIONS

Search Report and Written Opinion issued in International Patent Application No. PCT/US2021/024671, dated Aug. 5, 2021, 10 pages.
Brown, Amanda J et al. "A high-fat diet prevents and reverses the development of activity-based anorexia in rats." The International journal of eating disorders vol. 41,5 (2008): 383-9. doi:10.1002/eat.20510.
Chen, Yi-Wen et al. "Single injection of ketamine during mid-adolescence promotes long-lasting resilience to activity-based anorexia of female mice by increasing food intake and attenuating hyperactivity as well as anxiety-like behavior." The International journal of eating disorders vol. 51,8 (2018): 1020-1025. doi:10.1002/eat.22937.
Dutheil, Sophie et al. "High-Fat Diet Induced Anxiety and Anhedonia: Impact on Brain Homeostasis and Inflammation." Neuropsychopharmacology : official publication of the American College of Neuropsychopharmacology vol. 41,7 (2016): 1874-87. doi:10.1038/npp.2015.357.
Guisinger, Shan. "Adapted to flee famine: adding an evolutionary perspective on anorexia nervosa." Psychological review vol. 110,4 (2003): 745-61. doi: 10.1037/0033-295X.
Guisinger, Shan. Anorexia Nervosa: A Guide for Patients and Their Loved Ones. 110.4.745 (2007).
Kavalali, Ege T, and Lisa M Monteggia. "How does ketamine elicit a rapid antidepressant response ?." Current opinion in pharmacology vol. 20 (2015): 35-9. doi:10.1016/j.coph.2014.11.005.
Mills, I H et al. "Treatment of compulsive behaviour in eating disorders with intermittent ketamine infusions." QJM : monthly journal of the Association of Physicians vol. 91,7 (1998): 493-503. doi:10.1093/gjmed/91.7.493.
Taylor, J Andrew. NIH grant: "Heart Rate Variability as a Biomarker for Anorexia Nervosa". Submitted Feb. 12, 2019.
Scolnick, Barbara. "Ketogenic diet and anorexia nervosa." Medical hypotheses vol. 109 (2017): 150-152. doi:10.1016/j.mehy.2017.10.011.
Scolnick, Barbara et al. "Pilot study employing heart rate variability biofeedback training to decrease anxiety in patients with eating disorders." Journal of eating disorders vol. 2 17. Jun. 3, 2014, doi:10.1186/2050-2974-2-17.
Calabrese, Lori et al. "Ketogenic diet and ketamine infusion treatment to target chronic persistent eating disorder psychopathology in anorexia nervosa: a pilot study." Eating and weight disorders : EWD vol. 27,8 (2022): 3751-3757. doi:10.1007/s40519-022-01455-x.
Scolnick, Barbara et al. "Remission from Chronic Anorexia Nervosa With Ketogenic Diet and Ketamine: Case Report." Frontiers in psychiatry vol. 11 763. Jul. 30, 2020, doi: 10.3389/fpsyt.2020.00763.
Search Report and Written Opinion issued in International Patent Application No. PCT/US2021/024671, Aug. 5, 2021, 10 pages.

*Primary Examiner* — Paul V Ward
(74) *Attorney, Agent, or Firm* — Ballard Spahr

(57) ABSTRACT

The present disclosure relates generally to methods of treatment for eating disorders, such as anorexia nervosa and bulimia nervosa, and related clinical syndromes by maintaining a subject in need of treatment on a ketogenic diet and administering a ketamine to the subject.

21 Claims, No Drawings

METHODS OF TREATMENT FOR ANOREXIA NERVOSA, BULIMIA AND RELATED CLINICAL SYNDROMES

CROSS-REFERENCE TO RELATED APPLICATIONS

This application claims priority to U.S. Provisional Application No. 63/000,786 filed on Mar. 27, 2020, the entire content of which is incorporated by reference herein in its entirety.

FIELD OF THE DISCLOSURE

The present disclosure relates generally to methods of treatment for eating disorders, such as anorexia nervosa and bulimia nervosa, and related clinical syndromes by maintaining a subject in need of treatment on a ketogenic diet and administering a ketamine to the subject.

BACKGROUND OF THE DISCLOSURE

Eating disorders are very serious illnesses characterized by severe disturbances in eating, weight, body image and exercise. Because these neurobehavioral disorders have long been considered "mental" disorders, the task of defining and characterizing them has fallen to the field of psychiatry. The Diagnostic and Statistical Manual of Mental Disorders (DSM) is a decades long ongoing attempt by the American Psychiatric Association to define specific "mental disorders." Since the etiology and pathogenesis of eating disorders is unknown, criteria are in a state of flux, and with every rendition of the DSM, the criteria are somewhat altered. According to the most recent DSM published in 2013, and since it is the fifth rendition, known as the DSM-V, eating disorders are organized into 4 general categories: anorexia nervosa which is the most stereotypical and most deadly, bulimia nervosa, binge eating disorder, and "other" disorders that are more rare including pica, rumination disorder, and avoidant/restrictive food intake disorder.

According to the DSM-V, anorexia nervosa is marked by three features: (1) restriction of energy intake relative to requirements, leading to a significantly low body weight; (2) intense fear of gaining weight; and (3) disturbance in the way in which one's body weight is experienced. Bulimia nervosa, on the other hand, is marked by five features: (1) recurrent episodes of binge eating; (2) recurrent inappropriate compensatory behaviors in order to prevent weight gain such as self-induced vomiting; (3) occurrence of the binge or the compensatory behaviors at least once/week for 3 months; (4) self-evaluation is unduly influenced by body weight and size; and (5) behaviors do not occur exclusively during episodes of anorexia nervosa. While these two eating disorders are categorized separately, there is overlap, as a fairly high percentage (estimated to be ⅓) of patients will meet criteria for anorexia nervosa at the onset of the illness, and after several years will transition to a bulimia nervosa phenotype.

Although eating disorders can affect people of any gender at any life stage, they are most often reported in adolescents and young women. According to one statistic, up to about 13% of youth may experience at least one eating disorder by the age of 20.

No treatment has ever been found to be consistently successful. In recent years however, treatment has improved as emphasis has been on including the family in refeeding the patient (known as Family Based therapy or Maudsley Method) and starting refeeding as soon as the diagnosis is made. Yet the refeeding process is arduous, and there is no guarantee of success. Although estimates vary, the relapse rate is close to 40%, and once the disease becomes chronic the morbidity and mortality is quite high. Treatment options remain very limited, and no pharmacological agent has been definitely shown to improve the course or outcome.

Eating disorders can cause serious health consequences and may even result in death if left untreated. For instance, about 20% of anorexia nervosa patients will die, by far the highest death rate in any relatively common disease which affects young women, if left untreated. More than half of anorexia nervosa patients never properly recover and have some form of lifetime eating disorder which seriously disrupts their lives.

SUMMARY OF THE DISCLOSURE

Described herein are methods of treatment for eating disorders, such as anorexia nervosa and bulimia nervosa, and related clinical syndromes, using a combination of ketogenic diet and administration of ketamine or one of its analogs, pharmaceutically acceptable salts, derivatives or metabolites.

In one aspect, the disclosure relates to a method of treating anorexia nervosa, bulimia and related clinical syndromes in a subject in need thereof, said method comprising: a) placing the subject on a ketogenic diet and maintaining the subject on the ketogenic diet for a period of time sufficient to cause a detectable increase in ketone levels above levels associated without a ketogenic diet; and b) administering an effective amount of a pharmaceutical composition comprising ketamine, a ketamine analog, or a pharmaceutically acceptable salt, derivative, or metabolite thereof, to the subject, wherein combination of the ketogenic diet and administration of the pharmaceutical composition comprising ketamine, the ketamine analog, or the pharmaceutically acceptable salt, derivative, or metabolite thereof, is effective to treat said anorexia nervosa, bulimia and related clinical syndromes in the subject.

In some embodiments, the ketone levels are detected in blood, urine or breath. In some embodiments, the subject has a blood ketone level of from about 0.3 mmol/L to about 3.0 mmol/L of β-hydroxybutyrate prior to receiving the pharmaceutical composition comprising ketamine, the ketamine analog, or the pharmaceutically acceptable salt, derivative, or metabolite thereof. In some embodiments, the subject has a blood ketone level of from about 1.5 mmol/L to about 3.0 mmol/L of β-hydroxybutyrate prior to receiving the pharmaceutical composition comprising ketamine, the ketamine analog, or the pharmaceutically acceptable salt, derivative, or metabolite thereof.

In some embodiments, the ketogenic diet restricts meals taken by the subject to comprise fats and proteins/carbohydrates in a ratio of about 4:1 by weight. In some embodiments, the ketogenic diet restricts meals taken by the subject to comprise fats and proteins/carbohydrates in a ratio of about 3:1 by weight. In some embodiments, the ketogenic diet restricts meals taken by the subject to comprise fats and proteins/carbohydrates in a ratio of about 2:1 by weight. In some embodiments, the ketogenic diet restricts meals taken by the subject to comprise fats and proteins/carbohydrates in a ratio of about 1:1 by weight. In some embodiments, the ketogenic diet is a Modified Atkins diet comprising about 65% calories from fats, about 5% calories from carbohydrates, and about 30% calories from proteins. In some embodiments, the ketogenic diet is a Low Glycemic Load diet comprising about 60% calories from fats, about 10% calories from carbohydrates, and about 30% calories from proteins, wherein the carbohydrates taken by the subject have a glycemic index of less than about 50.

In some embodiments, the period of time in which the subject is maintained on the ketogenic diet is at least about 2 weeks. In some embodiments, the period of time in which the subject is maintained on the ketogenic diet is at least about 1 month. In some embodiments, the period of time in which the subject is maintained on the ketogenic diet is at least about 3 months.

In some embodiments, the pharmaceutical composition comprises esketamine, arketamine, and/or a racemic mixture of esketamine and arketamine. In some embodiments, the pharmaceutical composition is administered to the subject intravenously, orally, transdermally, intranasally, intramuscularly, intrathecally, or subcutaneously. In some embodiments, the pharmaceutical composition is administered to the subject by infusion.

In some embodiments, the effective amount of the pharmaceutical composition administered to the subject is from about 0.01 mg/kg to about 3 mg/kg body weight. In some embodiments, the effective amount of the pharmaceutical composition administered to the subject is from about 0.75 mg/kg to about 1.5 mg/kg body weight.

In some embodiments, the subject is administered with only one dose of the pharmaceutical composition. In some embodiments, the subject is administered with more than one dose of the pharmaceutical composition. In some embodiments, the subject is administered with an initial dose of the pharmaceutical composition comprising a first amount of ketamine, the ketamine analog, or the pharmaceutically acceptable salt, derivative, or metabolite thereof, followed by one or more doses of the pharmaceutical composition comprising a second amount of ketamine, the ketamine analog, or the pharmaceutically acceptable salt, derivative, or metabolite thereof, wherein the second amount of ketamine is greater than the first amount of ketamine. In some embodiments, the subject is administered with an initial dose of the pharmaceutical composition comprising a first amount of ketamine, the ketamine analog, or the pharmaceutically acceptable salt, derivative, or metabolite thereof, followed by one or more doses of the pharmaceutical composition comprising a second amount of ketamine, the ketamine analog, or the pharmaceutically acceptable salt, derivative, or metabolite thereof, wherein the second amount of ketamine is less than the first amount of ketamine. In certain embodiments, the subject is kept on a maintenance dose of ketamine, the ketamine analog or the pharmaceutical acceptable salt, derivative, or metabolite thereof.

In another aspect, the disclosure relates to a method of treating anorexia nervosa, bulimia and related clinical syndromes in a subject in need thereof, said method comprising: a) placing the subject on a ketogenic diet and maintaining the subject on the ketogenic diet for a period of time sufficient to cause a detectable increase in ketone levels above levels associated without a ketogenic diet; and b) administering an effective amount of a pharmaceutical composition comprising an antagonist of the glutamate N-methyl-D-aspartate (NMDA) receptor, wherein combination of the ketogenic diet and administration of the pharmaceutical composition comprising an antagonist of the glutamate N-methyl-D-aspartate (NMDA) receptor is effective to treat said anorexia nervosa, bulimia and related clinical syndromes in the subject.

In some embodiments, the antagonist of the NMDA receptor comprises ketamine, a ketamine analog, or a pharmaceutically acceptable salt, derivative, or metabolite thereof.

In yet another aspect, the disclosure relates to a method of treating anorexia nervosa, bulimia and related clinical syndromes in a subject in need thereof, said method comprising: a) administering an effective amount of a pharmaceutical composition comprising ketamine, a ketamine analog, or a pharmaceutically acceptable salt, derivative, or metabolite thereof, to the subject; and b) placing the subject on a ketogenic diet and maintaining the subject on the ketogenic diet for a period of time sufficient to cause a detectable increase in ketone levels above levels associated without a ketogenic diet, wherein combination of administration of the pharmaceutical composition comprising ketamine, the ketamine analog, or the pharmaceutically acceptable salt, derivative, or metabolite thereof, and the ketogenic diet is effective to treat said anorexia nervosa, bulimia and related clinical syndromes in the subject.

In some embodiments, the ketogenic diet restricts meals taken by the subject to comprise fats and proteins/carbohydrates in a ratio of about 4:1 by weight. In some embodiments, the ketogenic diet restricts meals taken by the subject to comprise fats and proteins/carbohydrates in a ratio of about 3:1 by weight. In some embodiments, the ketogenic diet restricts meals taken by the subject to comprise fats and proteins/carbohydrates in a ratio of about 2:1 by weight. In some embodiments, the ketogenic diet restricts meals taken by the subject to comprise fats and proteins/carbohydrates in a ratio of about 1:1 by weight. In some embodiments, the ketogenic diet is a Modified Atkins diet comprising about 65% calories from fats, about 5% calories from carbohydrates, and about 30% calories from proteins. In some embodiments, the ketogenic diet is a Low Glycemic Load diet comprising about 60% calories from fats, about 10% calories from carbohydrates, and about 30% calories from proteins, wherein the carbohydrates taken by the subject have a glycemic index of less than about 50.

In some embodiments, the ketone levels are detected in blood, urine or breath. In some embodiments, the ketogenic diet results in a blood ketone level of from about 0.3 mmol/L to about 3.0 mmol/L of β-hydroxybutyrate in the subject. In some embodiments, the ketogenic diet results in a blood ketone level of from about 1.5 mmol/L to about 3.0 mmol/L of β-hydroxybutyrate in the subject.

In some embodiments, the pharmaceutical composition comprises ketamine in a form selected from esketamine, arketamine, and/or a racemic mixture of esketamine and arketamine. In some embodiments, the pharmaceutical composition is administered to the subject intravenously, orally, transdermally, intranasally, intramuscularly, intrathecally, or subcutaneously. In some embodiments, the pharmaceutical composition is administered to the subject by infusion.

In some embodiments, the effective amount of the pharmaceutical composition comprising ketamine, the ketamine analog, or the pharmaceutically acceptable salt, derivative, or metabolite thereof, administered to the subject is from about 0.01 mg/kg to about 3 mg/kg body weight. In some embodiments, the effective amount of the pharmaceutical composition comprising ketamine, the ketamine analog, or the pharmaceutically acceptable salt, derivative, or metabolite thereof, administered to the subject is from about 0.75 mg/kg to about 1.5 mg/kg body weight.

DETAILED DESCRIPTION OF EMBODIMENTS

The present disclosure can be understood more readily by reference to the following detailed description of embodiments, the figures and the examples included herein.

Unless defined otherwise, all technical and scientific terms used herein have the same meaning as commonly understood by one of ordinary skill in the art to which the present disclosure pertains.

Definitions

As used in the specification and in the claims, the term "comprising" can include the aspects "consisting of" and "consisting essentially of" Comprising can also mean "including but not limited to."

As used in the specification and the appended claims, the singular forms "a," "an" and "the" can include plural referents unless the context clearly dictates otherwise. Thus, for example, reference to "a compound" includes mixtures of compounds; reference to "a pharmaceutical carrier" includes mixtures of two or more such carriers, and the like.

The word "or" as used herein means any one member of a particular list and also includes any combination of members of that list.

The term "about" is used herein to mean within the typical ranges of tolerances in the art. For example, "about" can be understood as about 2 standard deviations from the mean. According to certain embodiments, when referring to a measurable value such as an amount and the like, "about" is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value as such variations are appropriate to perform the disclosed methods. When "about" is present before a series of numbers or a range, it is understood that "about" can modify each of the numbers in the series or range.

The term "subject" used herein refers to a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child and adolescent, whether male or female, are intended to be covered. In some embodiments, the subject is one in need of treatment for an underlying disease or disorder, such as but not limited to anorexia nervosa, bulimia nervosa, and related clinical syndromes. In some embodiments, the subject being treated by any of the methods disclosed herein is diagnosed with or suspected of having chronic anorexia nervosa.

As used herein, the term "patient" refers to a subject afflicted with a disease or disorder. The term "patient" includes human and veterinary subjects. In some aspects of the disclosed methods, the "patient" has been diagnosed with a need for treatment for AN, bulimia and related clinical syndromes, such as, for example, prior to the administering step.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof.

The terms "treatment" or "treating" as used herein is an approach for obtaining beneficial or desired results including clinical results for the subject. For purposes herein, beneficial or desired clinical results include, but are not limited to, one or more of the following: (1) preventing or delaying the appearance of clinical symptoms of the state, disorder, or condition developing in a person who may be afflicted with or predisposed to the state, disorder or condition but does not yet experience or display clinical symptoms of the state, disorder or condition; (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The terms "severe and enduring anorexia nervosa," "chronic anorexia nervosa" and "chronic anorexia" are used herein interchangeably and are defined as having symptoms of anorexia nervosa persisting for a long period of time despite treatment. In some embodiments, severe and enduring anorexia nervosa, or chronic anorexia nervosa, in adults refers to having symptoms persisting for at least about 3 years despite treatment involving at least 2 modalities, such as different forms of therapy.

Ketogenic Diet

The ketogenic diet, or keto or KD for short, was developed about 100 years ago after the observation that prolonged fasting has anticonvulsive properties. The ketogenic diet is a way of eating that mimics the effects of fasting. By consuming a diet rich in quality fats, adequate in protein, and low in net carbohydrates (total carbs minus fiber), the body's metabolism begins to utilize fat as its main source of fuel. While metabolism is complicated, a simplified explanation begins with understanding that all the foods we eat can be categorized as either protein, carbohydrate, or fat. All are important, and different organs utilize different nutrient classes for energy source. The brain, for instance, cannot use fat as an energy source and thus, is dependent on glucose. However, a remarkable adaptation allows the brain to utilize ketone bodies, which are byproducts of fatty acid metabolism. Thus, although the brain cannot use fatty acids, it can use ketone bodies as an energy source. This adaptation has allowed humans to survive episodes of starvation or famine. Ketone bodies are natural products of fat metabolism. If glucose is undersupplied (either from famine, or from limiting glucose in the diet), the body starts to increase metabolism of fatty acids. In the case of starvation, the fatty acids are coming from the stored adipose tissue; in the case of a ketogenic diet, the fatty acids are coming from the nutrients ingested. In either case, the β-oxidation, or metabolic breakdown of fatty acids, leads to an accumulation of acetyl CoA. The acetyl CoA filters into the Krebs cycle and ATP is formed. However, if fatty acid β-oxidation is vastly increased (due to starvation or a ketogenic diet), the Krebs cycle gets overwhelmed and the excess acetyl CoA gets diverted into three chemicals known as "ketone bodies": β-hydroxybutyrate, acetoacetate, and acetone. Ketosis is generally accepted as meaning a blood β-hydroxybutyrate is greater than 0.3 m Mol/L.

Achieving a state of ketosis can have many benefits from treating chronic illnesses to optimizing both mental and physical performance. Studies have been published showing therapeutic benefits of the ketogenic diet for a variety of diseases. For instance, a ketogenic diet has been shown to be an effective alternative when treating refractory epilepsy and albeit its mechanisms are still poorly understood, there is mounting experimental evidence for its broad neuro-protective mechanisms and its potential use in multiple neurological disease states, for example metabolic defects, such as mitochondrial disorders, neurodegenerative disorders, such as Parkinson's disease and Alzheimer's disease, trauma and ischemia, narcolepsy and maybe even depression or autism. While the benefits are well documented, the underlying mechanism of action is not entirely clear. The diet seems to enhance the ability of mitochondria, the power plants of our cells, to deliver our bodies' energy needs in a manner that reduces inflammation and oxidative stress.

Accordingly, as used herein, the term "ketogenic diet," "keto" or "KD" refers to a diet with high fat content, low carbohydrate, and varying protein content. A ketogenic diet may vary from very strict to relatively lax, and the determining feature is the ratio of (fat in grams) to (protein+carbohydrates in grams). Traditionally, the diet used for seizure patients has been a very severe 4:1 ratio, which means 4 grams of fat to every 1 gram of (carbohydrate+protein). Since one gram of fat is equivalent to 9 calories, one gram of carbohydrate is equivalent to 4 calories, and one gram of protein is equivalent to 4 calories, this 4:1 ratio calculates to about 90% of the calories coming from fat. In the modern era of KD therapy (since 1994), more liberal diets have also been shown to be effective, which include the following modified ketogenic diets:

- 3:1 ratio KD diet, meaning 3 grams of fat to every gram of protein+carbohydrates, which equals to about 87% calories from fat;
- 2:1 ratio KD diet, meaning 2 grams of fat to every gram of protein+carbohydrates, which equals to about 82% calories from fat, about 6% calories from carbohydrate, and about 12% calories from protein;
- 1:1 ratio KD diet, meaning 1 gram of fat to every gram of protein+carbohydrates, which equals to about 70% calories from fat, about 15% calories from carbohydrates, and 15% calories from protein;
- Modified Atkins diet with about 65% calories from fat, about 5% calories from carbohydrates, and about 30% calories from protein; and
- Low Glycemic Load diet with about 60% calorie from fat, about 10% calorie from carbohydrates, and about 30% calorie from protein. The carbohydrates in this diet must be those with a glycemic index of less than 50. Glycemic index is a measure of how quickly the blood sugar rises after ingestion.

Compared to the KD or modified KD diets, in the typical American diet, about 35% calories are obtained from fat, about 50% calories from carbohydrates, and about 15% calories from protein. It is important to note that, while about 50% of calories are obtained from carbohydrates in the typical American diet, many patients with anorexia nervosa avoid both fats and protein, and thus their diet is much higher in carbohydrate content.

In practical terms, as long as mild-moderate ketosis is being induced, and the subject is starting to experience relief from symptoms, it is not necessary to be compulsive about maintaining a specific ratio. The guidelines for ketogenic diet are summarized in online and print literature from the Charlie Foundation for Ketogenic Therapies (charliefoundation.org), a not-for-profit organization started in 1994 with mission to increase awareness of this diet as alternative treatment for certain diseases or disorders.

In some embodiments therefore, the ketogenic diet used in the methods of the disclosure refers to a diet with meals comprising fats (in grams) and proteins/carbohydrates (in grams) in a ratio of about 4:1, 3.5:1, 3:1, 2.5:1, 2:1, 1.5:1, or 1:1. In some embodiments, the ketogenic diet used in the methods of the disclosure refers to a diet with meals comprising fats (in grams) and proteins/carbohydrates (in grams) in a ratio of about 4:1. In some embodiments, the ketogenic diet used in the methods of the disclosure refers to a diet with meals comprising fats (in grams) and proteins/carbohydrates (in grams) in a ratio of about 3.5:1. In some embodiments, the ketogenic diet used in the methods of the disclosure refers to a diet with meals comprising fats (in grams) and proteins/carbohydrates (in grams) in a ratio of about 3:1. In some embodiments, the ketogenic diet used in the methods of the disclosure refers to a diet with meals comprising fats (in grams) and proteins/carbohydrates (in grams) in a ratio of about 2.5:1. In some embodiments, the ketogenic diet used in the methods of the disclosure refers to a diet with meals comprising fats (in grams) and proteins/carbohydrates (in grams) in a ratio of about 2:1. In some embodiments, the ketogenic diet used in the methods of the disclosure refers to a diet with meals comprising fats (in grams) and proteins/carbohydrates (in grams) in a ratio of about 1.5:1. In some embodiments, the ketogenic diet used in the methods of the disclosure refers to a diet with meals comprising fats (in grams) and proteins/carbohydrates (in grams) in a ratio of about 1:1.

In some embodiments, the ketogenic diet used in the methods of the disclosure refers to a diet with meals comprising about 5%, 10%, 15% or 20% by weight of carbohydrates, about 30%, 35%, 40%, 45% or 50% by weight of proteins, and about 40%, 45%, 50%, 55%, 60%, 65%, 75% or 80% by weight of fats. In some embodiments, the ketogenic diet used in the methods of the disclosure refers to a diet with meals comprising about 5% by weight of carbohydrates, about 15% by weight of proteins, and about 80% by weight of fats. In some embodiments, the ketogenic diet used in the methods of the disclosure refers to a diet with meals comprising about 10% by weight of carbohydrates, about 15% by weight of proteins, and about 75% by weight of fats. In some embodiments, the ketogenic diet used in the methods of the disclosure refers to a diet with meals comprising about 15% by weight of carbohydrates, about 25% by weight of proteins, and about 60% by weight of fats. In some embodiments, the ketogenic diet used in the methods of the disclosure refers to a diet with meals comprising about 15% by weight of carbohydrates, about 30% by weight of proteins, and about 55% by weight of fats. In some embodiments, the ketogenic diet used in the methods of the disclosure refers to a diet with meals comprising about 15% by weight of carbohydrates, about 35% by weight of proteins, and about 50% by weight of fats. In some embodiments, the ketogenic diet used in the methods of the disclosure refers to a diet with meals comprising about 10% by weight of carbohydrates, about 45% by weight of proteins, and about 45% by weight of fats.

In some embodiments, the ketogenic diet used in the methods of the disclosure refers to a diet in which about 90% of the calories coming from fat. In some embodiments, the ketogenic diet used in the methods of the disclosure refers to a diet in which about 85% of the calories coming from fat. In some embodiments, the ketogenic diet used in the methods of the disclosure refers to a diet in which about 80% of the calories coming from fat. In some embodiments, the ketogenic diet used in the methods of the disclosure refers to a diet in which about 75% of the calories coming from fat. In some embodiments, the ketogenic diet used in the methods of the disclosure refers to a diet in which about 70% of the calories coming from fat. In some embodiments, the ketogenic diet used in the methods of the disclosure refers to a diet in which about 65% of the calories coming from fat. In some embodiments, the ketogenic diet used in the methods of the disclosure refers to a diet in which about 60% of the calories coming from fat.

In some embodiments, the ketogenic diet used in the methods of the disclosure refers to a Modified Atkins diet with about 65% calories from fats, about 5% calories from carbohydrates, and about 30% calories from proteins. In some embodiments, the ketogenic diet used in the methods of the disclosure refers to a Low Glycemic Load diet with about 60% calories from fats, about 10% calories from carbohydrates, and about 30% calories from proteins. In such embodiments where the subject is maintained with a Low Glycemic Load diet, the carbohydrates must be those with a glycemic index of less than 50. Glycemic index is a measure of how quickly the blood sugar rises after ingestion.

The ketogenic diet of the methods of the disclosure is used to induce nutritional ketosis and avoid the ketosis of starvation. The term "ketosis" refers to a byproduct of the breakdown of fat into useable energy, called ketones. Ketones are alternative energy sources for both the brain and body. This fat can be derived directly from the food we eat, known as nutritional ketosis, or from stored body fat. Nutritional ketosis results when fat is the main source of calories and usually results in a mid-level of blood ketones (or serum β-hydroxybutyrate) of about 0.3-3 mmol/L. Ketone levels can be compared either to the subject's own baseline pre-ketogenic diet levels, or compared to average normal non-ketogenic diet values. Thus, in some embodiments, the methods of the disclosure comprise measuring ketone levels of the subject prior to placing the subject on a ketogenic diet and use the measured level as a baseline to determine whether the subject has a detectable increase in ketone levels. In other embodiments, whether the subject has a detectable increase in ketone levels is determined by comparing the subject's ketone levels to average normal non-ketogenic diet values.

Ketone levels may be measured using any methods known in the art and any apparatuses available in the markets. There are three ways to measure ketones in a human body. Measuring ketones present in the blood using a blood ketone meter is the most accurate, but also the most expensive way to measure ketone levels. Both acetoacetate (the first ketone that is generated from fatty acids) and β-hydroxybutyrate (converted from acetoacetate) can be detected in the blood, but usually β-hydroxybutyrate is measured. Measuring ketones present in the urine using a urine stick is an alternative, cheaper and easy way to measure ketone levels, but it tends to be not very accurate. This type of measurement measures acetoacetate and the volatile acetone. However, urine sticks measures the ketone level qualitatively rather than quantitatively, which means that the measurement is generally records as "0" to "+4" and indicated by a color change from, for example, pale white to purple, with darker color as being higher ketone level. While the correlation is not perfect, roughly "+1" means a ketone level of about 4 mmol/L of acetoacetate and acetone and "+4" means a ketone level of about 16 mmol/L of acetoacetate and acetone. Ketone levels can also be measured by measuring breath acetone levels with a portable breath meter, which is generally considered to be more accurate than using urine sticks. While certain types of breath meters measure the ketone level qualitatively rather than quantitatively similar to urine sticks, some can actually measure the ketone level quantitatively. With this type of breath meters, it is generally considered to be a high ketone level when the reading is about 100-150 nmol/L, a moderate or medium ketone level when the reading is about 50-100 nmol/L, and a low ketone level when the reading is about 0-50 nmol/L.

Thus, in some embodiments, the ketogenic diet used in the methods of the disclosure refers to a high fat/low carb diet that induces a blood ketone level from about 0.3 mmol/L to about 3.0 mmol/L of β-hydroxybutyrate. In some embodiments, the ketogenic diet used in the methods of the disclosure refers to a high fat/low carb diet that induces a blood ketone level from about 0.5 mmol/L to about 3.0 mmol/L of β-hydroxybutyrate. In some embodiments, the ketogenic diet used in the methods of the disclosure refers to a high fat/low carb diet that induces a blood ketone level from about 1.0 mmol/L to about 3.0 mmol/L of β-hydroxybutyrate. In some embodiments, the ketogenic diet used in the methods of the disclosure refers to a high fat/low carb diet that induces a blood ketone level from about 1.5 mmol/L to about 3.0 mmol/L of β-hydroxybutyrate. In some embodiments, the ketogenic diet used in the methods of the disclosure refers to a high fat/low carb diet that induces a blood ketone level from about 2.0 mmol/L to about 3.0 mmol/L of β-hydroxybutyrate. In some embodiments, the ketogenic diet used in the methods of the disclosure refers to a high fat/low carb diet that induces a blood ketone level from about 2.5 mmol/L to about 3.0 mmol/L of β-hydroxybutyrate.

In some embodiments, the ketogenic diet used in the methods of the disclosure refers to a high fat/low carb diet that induces a blood ketone level of about 0.6 mmol/L of 3-hydroxybutyrate. In some embodiments, the ketogenic diet used in the methods of the disclosure refers to a high fat/low carb diet that induces a blood ketone level of about 0.7 mmol/L of 3-hydroxybutyrate. In some embodiments, the ketogenic diet used in the methods of the disclosure refers to a high fat/low carb diet that induces a blood ketone level of about 0.8 mmol/L of 3-hydroxybutyrate. In some embodiments, the ketogenic diet used in the methods of the disclosure refers to a high fat/low carb diet that induces a blood ketone level of about 0.9 mmol/L of 3-hydroxybutyrate. In some embodiments, the ketogenic diet used in the methods of the disclosure refers to a high fat/low carb diet that induces a blood ketone level of about 1.0 mmol/L of β-hydroxybutyrate. In some embodiments, the ketogenic diet used in the methods of the disclosure refers to a high fat/low carb diet that induces a blood ketone level of about 1.1 mmol/L of β-hydroxybutyrate. In some embodiments, the ketogenic diet used in the methods of the disclosure refers to a high fat/low carb diet that induces a blood ketone level of about 1.2 mmol/L of β-hydroxybutyrate. In some embodiments, the ketogenic diet used in the methods of the disclosure refers to a high fat/low carb diet that induces a blood ketone level of about 1.3 mmol/L of β-hydroxybutyrate. In some embodiments, the ketogenic diet used in the methods of the disclosure refers to a high fat/low carb diet that induces a blood ketone level of about 1.4 mmol/L of β-hydroxybutyrate. In some embodiments, the ketogenic diet used in the methods of the disclosure refers to a high fat/low carb diet that induces a blood ketone level of about 1.5 mmol/L of β-hydroxybutyrate. In some embodiments, the ketogenic diet used in the methods of the disclosure refers to a high fat/low carb diet that induces a blood ketone level of about 1.6 mmol/L of β-hydroxybutyrate. In some embodiments, the ketogenic diet used in the methods of the disclosure refers to a high fat/low carb diet that induces a blood ketone level of about 1.7 mmol/L of β-hydroxybutyrate. In some embodiments, the ketogenic diet used in the methods of the disclosure refers to a high fat/low carb diet that induces a blood ketone level of about 1.8 mmol/L of β-hydroxybutyrate. In some embodiments, the ketogenic diet used in the methods of the disclosure refers to a high fat/low carb diet that induces a blood ketone level of about 1.9 mmol/L of β-hydroxybutyrate. In some embodiments, the ketogenic diet used in the methods of the disclosure refers to a high fat/low carb diet that induces a blood ketone level of about 2.0 mmol/L of β-hydroxybutyrate. In some embodiments, the ketogenic diet used in the methods of the disclosure refers to a high fat/low carb diet that induces a blood ketone level of about 2.1 mmol/L of β-hydroxybutyrate. In some embodiments, the ketogenic diet used in the methods of the disclosure refers to a high fat/low carb diet that induces a blood ketone level of about 2.2 mmol/L of β-hydroxybutyrate. In some embodiments, the ketogenic diet used in the methods of the disclosure refers to a high fat/low carb diet that induces a blood ketone level of about 2.3 mmol/L of β-hydroxybutyrate. In some embodiments, the ketogenic diet used in the methods of the disclosure refers to a high fat/low carb diet that induces a blood ketone level of about 2.4 mmol/L of β-hydroxybutyrate. In some embodiments, the ketogenic diet used in the methods of the disclosure refers to a high fat/low carb diet that induces a blood ketone level of about 2.5 mmol/L of β-hydroxybutyrate. In some embodiments, the ketogenic diet used in the methods of the disclosure refers to a high fat/low carb diet that induces a blood ketone level of about 2.6 mmol/L of β-hydroxybutyrate. In some embodiments, the ketogenic diet used in the methods of the disclosure refers to a high fat/low carb diet that induces a blood ketone level of about 2.7 mmol/L of β-hydroxybutyrate. In some embodiments, the ketogenic diet used in the methods of the disclosure refers to a high fat/low carb diet that induces a blood ketone level of about 2.8 mmol/L of β-hydroxybutyrate. In some embodiments, the ketogenic diet used in the methods of the disclosure refers to a high fat/low carb diet that induces a blood ketone level of about 2.9 mmol/L of β-hydroxybutyrate. In some embodiments, the ketogenic diet used in the methods of the disclosure refers to a high fat/low carb diet that induces a blood ketone level of about 3.0 mmol/L of β-hydroxybutyrate.

In some embodiments, the ketogenic diet used in the methods of the disclosure refers to a high fat/low carb diet that induces a "+1" level of ketone as measured by a urine stick. In some embodiments, the ketogenic diet used in the methods of the disclosure refers to a high fat/low carb diet that induces a "+2" level of ketone as measured by a urine stick. In some embodiments, the ketogenic diet used in the methods of the disclosure refers to a high fat/low carb diet that induces a "+3" level of ketone as measured by a urine stick.

In some embodiments, the ketogenic diet used in the methods of the disclosure refers to a high fat/low carb diet that induces at least a low ketone level as measured by a breath meter. In some embodiments, the ketogenic diet used in the methods of the disclosure refers to a high fat/low carb diet that induces at least a medium or moderate ketone level as measured by a breath meter. In some embodiments, the ketogenic diet used in the methods of the disclosure refers to a high fat/low carb diet that induces at least a high ketone level as measured by a breath meter.

In some embodiments, the ketogenic diet used in the methods of the disclosure refers to a high fat/low carb diet that induces about 0-25 nmol/L of acetone as measured by a breath meter. In some embodiments, the ketogenic diet used in the methods of the disclosure refers to a high fat/low carb diet that induces about 25-50 nmol/L of acetone as measured by a breath meter. In some embodiments, the ketogenic diet used in the methods of the disclosure refers to a high fat/low carb diet that induces about 50-75 nmol/L of acetone as measured by a breath meter. In some embodiments, the ketogenic diet used in the methods of the disclosure refers to a high fat/low carb diet that induces about 75-100 nmol/L of acetone as measured by a breath meter. In some embodiments, the ketogenic diet used in the methods of the disclosure refers to a high fat/low carb diet that induces about 100-125 nmol/L of acetone as measured by a breath meter. In some embodiments, the ketogenic diet used in the methods of the disclosure refers to a high fat/low carb diet that induces about 125-150 nmol/L of acetone as measured by a breath meter.

N-methyl D-Aspartate (NMDA) Receptor Antagonists

NMDA receptor antagonists are a class of compounds that antagonize, or inhibit, the action of the NMDA receptor. An NMDA receptor antagonist may be a competitive antagonist, an uncompetitive antagonist, a noncompetitive antagonist, and/or a glycine antagonist. Non-limiting examples of NMDA receptor antagonists include, ketamine, dextromethorphan (DXM), histogranin, memantine, meperidine, methadone, methoxetainine (NIXE), phencyclidine (PCP), nitrous oxide ($N_2O$), AP5 (APV, R-2-amino-5-phosphonopentanoate), AP7 (2-amino-7-phosphonoheptimoic acid), CPPene ((3-[(R)-2-carboxypiperazin-4-yl]-prop-2-enyl-1-phosphonic acid), Selfotel, Amantadine, Atomoxetinc, AZD6765, Agmatine, chloroform, dextrallorphan, dextrorphan, diphenidine, dizocilpine (MK-801), ethanol, eticyclidine, gacyclidine, ibogaine, magnesium, memantine, nitromemantine, rolicyclidine, tenocyclidine, methoxydine, tiletamine. neramexane, eliprodil, dexoxadrol, etoxadrol, remacemide, delucemine, WMS-2539, NEFA, 8A-PDUQ, HU-211, Aptiganel (Cerestat, CNS-1102), rhynchophylline, kynurenic acid, Rapastinel (GLYX-13), NRX-1074, 7-Chlorokynurenic acid, 4-Chlorokynurenine (AV-101), TK-40, 1-Aminocyclopropanecartioxylic acid (ACPC), L-Phenylalanine, Xenon, or analogs or derivatives thereof. Non-limiting ketamine derivatives such as Rapastinel or Glyx-13 are also included. Rapastinel is an NMDA receptor glycine site partial agonist. It is an amidated tetrapeptide (Thr-Pro-Pro-Thr-$NH_2$) which rapidly crosses the blood brain barrier, but is not active orally.

Compounds that are mechanistically similar to ketamine are expected to be protective against stress-induced de novo psychopathology and thus, useful in the methods of the disclosure. Such compounds include:

Ro 25-6981, a GluN2B-selective antagonist (Miller et al., (2014), *eLife* 3:e03581), which has been shown to have rapid antidepressant actions in rodent models of depression;

CP-101,606, a GluN2B-selective antagonist (Preskom et al., (2007): A placebo-controlled trial of the NR2B specific NMDA antagonist CP-101, 606 plus paroxetine for treatment resistant depression (TRD). *American Psychological Association meeting*), which has been shown to be protective in animal models of brain injury and stroke;

GLYX-13, a novel N-methyl-D-aspartate receptor (NMDAR) glycine-site functional partial agonist and rapid-acting antidepressant (Burgdorf et al., (2013), *Neuropsychopharmacology* 38:729-42). GLYX-13 received Breakthrough Therapy designation from the U.S. Food and Drug Administration (FDA) for adjunctive treatment of MDD in January, 2016; and CX546 (Tocris), an ampakine (an AMPA receptor agonist) (Zhou et al, (2014), *Ear. Psychiatry* 29:419-23), which relieves the respiratory depression induced by fentanyl.

Non-limiting examples of the NMDA receptor antagonists also include anti-receptor antibodies, anti-ligand antibodies, etc. Several synthetic opioids function as NMDA receptor-antagonists, such as pethidine, methadone, meperidine, dextropropoxyphene, tramadol, levorphanol, and ketobemidone. All these compounds may also be used in the method of the disclosure.

Ketamine

Ketamine ((RS)-2-(2-chlorophenyl)-2-(methylamino)cyclohexanone) is an antagonist of the NMDA receptor (NMDAR). Ketamine also acts on opioid receptors, sigma-1 receptors, muscarinic receptors, monoamine transporters, etc.

Ketamine is a chiral compound. As used herein therefore, the term "ketamine" refers to interchangeably ketamine in all of its forms, including but not limited to its racemic form and all enantiomeric proportions of esketamine (S-ketamine or S-(+)-ketamine) and arketamine (R-ketamine or R-(−)-ketamine), including pure estakine and arketamine, or a racemic mixture of (S)-ketamine and (R)-ketamine, ketamine analogs, or pharmaceutically acceptable salts, derivatives, or metabolites thereof. The molecular structures of ketamine and its enantiomers are shown below:

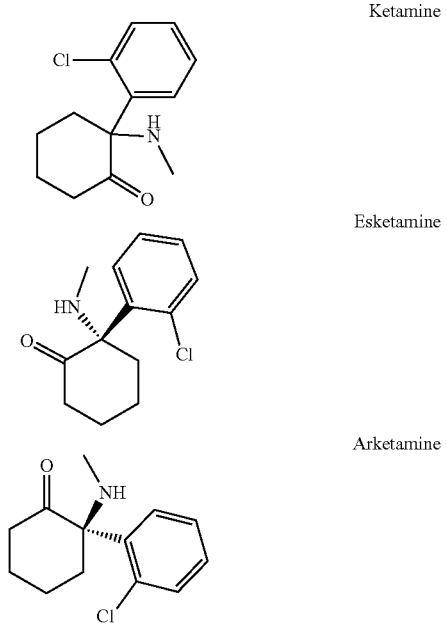

Ketamine

Esketamine

Arketamine

The compositions used in the methods of the present disclosure may comprise a compound in a salt form. As used herein, a "salt" is a salt of a compound which has been modified by making acid or base. In the case of compounds used for treatment of mammals, the salt should be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, henzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds comprised in the composition. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarase, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compositions used in the methods of the disclosure may comprise a pharmaceutically acceptable derivative of a compound. As used herein, the term "pharmaceutically acceptable derivative" refers to a compound (e.g., a drug precursor) that is transformed in vivo to yield the intended compound or its active metabolite, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

As used herein, the term "ketamine composition" refers to a pharmaceutical composition comprising ketamine, a ketamine analog, or a pharmaceutically acceptable salt, derivative, or metabolite thereof. In some embodiments, the ketamine compositions may comprise different proportions of the S(+) and R(−) stereoisomers. In some embodiments, the ketamine compositions comprise only (S)-ketamine or (R)-ketamine, or are enantiomerically enriched for a ketamine enantiomer. In some embodiments, the ketamine composition is enriched to comprise, for example, greater than about 60%, greater than about 70%, greater than about 80%, greater than about 90%, greater than about 95%, greater than about 99%, or greater than about 99.9 of (S)-ketamine or (R)-ketamine.

Ketamine is a derivative of arylcyclohexylamine. Since the 1950s, a large number of arylcyclohexylamines have been synthesized; these compounds have shown a wide range of possible pharmacological activities. When administered orally, it undergoes first-pass metabolism, where it is stereo selectively metabolized into a broad array of metabolites, including norketamine, hydroxyketamines, dehydronorketamine and hydmxynorketamine (HNK). After ketamine administration, (2S,6S;2R,6R)-HNK are the two major HNK metabolites found in the plasma and brain. Interestingly, a recent study has shown that the (2R,6R)-HNK metabolite is: 1) essential for the antidepressant effects of ketamine, 2) dependent on α-amino-3-hydroxy-5-methyl-4-isoxazolepropionic acid (AMPA) receptor activation, and 3) non-hypnotic (Zanos et al., Nature, 2016, 533: 481-486). All of these compounds are suitable for use in the presently described methods, including enantiomers and non-psychotomimetic metabolites of ketamine. Such compounds include:

(2R,6R)-HNK, a metabolite of ketamine that may mediate the antidepressant effects of ketamine and lacks the ketamine-related side effects (Zanos et al., Nature, 2016, 533: 481-486);

(2S,6S)-HNK, a metabolite of ketamine (Zanos et al., 2016; Wainer et al. WO 2013/056229 (2013)) used in the treatment of depression and neuropathic pain;

(R)-ketamine, the R-enantiomer of ketamine, which has rapid-onset and sustained antidepressant effects without psychotomimetic side effects (Yang et al., 2015); and (S)-ketamine, the S-enantiomer of ketamine, which is being developed as an intranasal spray and recently approved for treatment of resistant depression (also known as SPRAVATO® (esketamine) CIII Nasal Spray by Janssen Pharmaceuticals, Inc.).

In some embodiments therefore, the ketamine compositions used in the methods of the disclosure comprise one or more enantiomers of ketamine. In some embodiments, the ketamine compositions comprise one or more non-psychotomimetic metabolites of ketamine. In some embodiments, the ketamine compositions comprise ketamine. In some embodiments, the ketamine compositions comprise hydroxyketamines. In some embodiments, the ketamine compositions comprise dehydronorketamine. In some embodiments, the ketamine compositions comprise hydmxynorketamine (HNK). In some embodiments, the ketamine compositions comprise (2R,6R)-HNK. In some embodiments, the ketamine compositions comprise (2S,6S)-HNK. In some embodiments, the ketamine compositions comprise (S)-ketamine.

Other ketamine analogs are also expected to be effective in the methods of the disclosure. Such compounds include:
Fluorodeschloroketamine, an analog of ketamine where the chlorine (Cl) group has been replaced by fluorine (F); and
Tiletamine, an analog of ketamine commonly used as a veterinary anesthetic.

In some embodiments, the ketamine compositions used in the methods of the disclosure comprise fluorodeschloroketamine. In some embodiments, the ketamine compositions comprise tiletamine.

The term "pharmaceutically acceptable derivative" refers to any pharmaceutically acceptable salt, solvate or prodrug, e.g., ester, of a compound which upon administration to the recipient is capable of providing (directly or indirectly) a compound or an active metabolite or residue thereof. Such derivatives are recognizable to those skilled in the art, without undue experimentation. Derivatives are described, for example, in Burger's Medicinal Chemistry and Drug Discovery, 5$^{th}$ Edition, Vol 1: Principles and Practice, which is incorporated herein by reference. In some embodiments, pharmaceutically acceptable derivatives include salts, solvates, esters, carbamates, and phosphate esters. In some embodiments, the ketamine compositions used in the methods of the disclosure comprise a hydrochloride salt of ketamine.

As used herein, a "therapeutically effective amount" or "effective amount" of a compound or composition or combination refers to an amount effective, at dosages and for periods of time necessary, to achieve a desired therapeutic result, such as for treatment of a disease, condition, or disorder, and/or pharmacokinetic or pharmacodynamic effect of the treatment. The amount of composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. In some embodiments, an effective amount of ketamine, a ketamine analog, or a pharmaceutically acceptable salt, derivative, or metabolite thereof, is an amount effective to prevent or delay the onset of a stress-induced affective disorder, and/or effective to alleviate, one or more of the symptoms of a stress-induced affective disorder. In some embodiments, an effective amount of ketamine, a ketamine analog, or a pharmaceutically acceptable salt, derivative, or metabolite thereof, is an amount effective to prevent or delay the onset of an anorexia nervosa-induced affective disorder, and/or effective to alleviate, one or more of the symptoms of an anorexia nervosa-induced affective disorder. In some embodiments, an effective amount of ketamine, a ketamine analog, or a pharmaceutically acceptable salt, derivative, or metabolite thereof, is an amount effective to prevent or delay the onset of a bulimia nervosa-induced affective disorder, and/or effective to alleviate, one or more of the symptoms of a bulimia-induced affective disorder.

In some embodiments, an effective amount of the ketamine composition used in the methods of the disclosure comprises a sub-anesthetic amount of ketamine, a ketamine analog, or a pharmaceutically acceptable salt, derivative, or metabolite thereof. In some embodiments, an effective amount of the ketamine composition used in the methods of the disclosure comprises a sub-analgesic amount of ketamine, a ketamine analog, or a pharmaceutically acceptable salt, derivative, or metabolite thereof.

Ketamine, when administered in sub-anesthetic doses, is an effective treatment for severe and even treatment-refractory depression. In such uses, ketamine is most commonly administered in the dose of 0.5 mg/kg, but some patients may respond to doses as low as 0.1 mg/kg and others may require up to 0.75 mg/kg. In some embodiments therefore, an effective amount of the ketamine composition used in the methods of the disclosure comprises an amount of the ketamine composition equals to a dose of from about 0.01 mg/kg to about 3 mg/kg body weight. In some embodiments, an effective amount of the ketamine composition used in the methods of the disclosure comprises an amount of the ketamine composition equals to a dose of from about 0.75 mg/kg to about 1.5 mg/kg body weight. In some embodiments therefore, an effective amount of the ketamine composition used in the methods of the disclosure comprises an amount of the ketamine composition equals to a dose of about 0.1 mg/kg body weight. In some embodiments, an effective amount of the ketamine composition used in the methods of the disclosure comprises an amount of the ketamine composition equals to a dose of about 0.5 mg/kg body weight. In some embodiments, an effective amount of the ketamine composition used in the methods of the disclosure comprises an amount of the ketamine composition equals to a dose of about 0.75 mg/kg body weight. In some embodiments, an effective amount of the ketamine composition used in the methods of the disclosure comprises an amount of the ketamine composition equals to a dose of about 1.0 mg/kg body weight. In some embodiments, an effective amount of the ketamine composition used in the methods of the disclosure comprises an amount of the ketamine composition equals to a dose of about 1.2 mg/kg body weight. In some embodiments, an effective amount of the ketamine composition used in the methods of the disclosure comprises an amount of the ketamine composition equals to a dose of about 1.5 mg/kg body weight.

In some embodiments, an effective amount of the ketamine composition used in the methods of the disclosure is an amount effective to prevent or delay the onset of an anorexia nervosa-induced affective disorder, and/or effective to alleviate, one or more of the symptoms of an anorexia nervosa-induced affective disorder. In some embodiments, an effective amount of the ketamine composition used in the methods of the disclosure is an amount effective to prevent or delay the onset of a bulimia nervosa-induced affective disorder, and/or effective to alleviate, one or more of the symptoms of a bulimia-induced affective disorder. In some embodiments, an effective amount of ketamine composition used in the methods of the disclosure is an amount that is effective when administered to a subject maintained on a ketogenic diet.

The ketamine composition, a ketamine analog, or a pharmaceutically acceptable salt, derivative, or metabolite thereof, used in the methods of the disclosure may be administered by various routes, including intravenous (i.v. or IV), oral, transdermal, intranasal (i.n. or IN), intramuscular (i.m. or IM), intrathecal, and subcutaneous (s.c.) routes. In some embodiments, the ketamine composition, a ketamine analog, or a pharmaceutically acceptable salt, derivative, or metabolite thereof, is administered intravenously. In some embodiments, the ketamine composition, a ketamine analog, or a pharmaceutically acceptable salt, derivative, or metabolite thereof, is administered orally. In some embodiments, the ketamine composition, a ketamine analog, or a pharmaceutically acceptable salt, derivative, or metabolite thereof, is administered transdermally. In some embodiments, the ketamine composition, a ketamine analog, or a pharmaceutically acceptable salt, derivative, or metabolite thereof, is administered intranasally. In some embodiments, the ketamine composition, a ketamine analog, or a pharmaceutically acceptable salt, derivative, or metabolite thereof, is administered intramuscularly. In some embodiments, the ketamine composition, a ketamine analog, or a pharmaceutically acceptable salt, derivative, or metabolite thereof, is administered intrathecally. In some embodiments, the ketamine composition, a ketamine analog, or a pharmaceutically acceptable salt, derivative, or metabolite thereof, is administered subcutaneously. In some embodiments, the ketamine composition, a ketamine analog, or a pharmaceutically acceptable salt, derivative, or metabolite thereof, is administered by infusion.

In some embodiments, the ketamine composition, a ketamine analog, or a pharmaceutically acceptable salt, derivative, or metabolite thereof, is administered by an IV infusion over a period of time, such as about 10 minutes, about 20 minutes, about 30 minutes, about 40 minutes, about 50 minutes, or about 60 minutes. In some embodiments, the ketamine composition, a ketamine analog, or a pharmaceutically acceptable salt, derivative, or metabolite thereof, is administered by a 10-minute IV infusion. In some embodiments, the ketamine composition, a ketamine analog, or a pharmaceutically acceptable salt, derivative, or metabolite thereof, is administered by a 20-minute IV infusion. In some embodiments, the ketamine composition, a ketamine analog, or a pharmaceutically acceptable salt, derivative, or metabolite thereof, is administered by a 30-minute IV infusion. In some embodiments, the ketamine composition, a ketamine analog, or a pharmaceutically acceptable salt, derivative, or metabolite thereof, is administered by a 40-minute IV infusion. In some embodiments, the ketamine composition, a ketamine analog, or a pharmaceutically acceptable salt, derivative, or metabolite thereof, is administered by a 50-minute IV infusion. In some embodiments, the ketamine composition, a ketamine analog, or a pharmaceutically acceptable salt, derivative, or metabolite thereof, is administered by a 60-minute IV infusion.

In some embodiments, a subject is treated with a single dose of an effective amount of the ketamine composition, a ketamine analog, or a pharmaceutically acceptable salt, derivative, or metabolite thereof, prior to and/or after adopting a ketogenic diet. In some embodiments, a subject is treated with multiple doses of an effective amount of the ketamine composition, a ketamine analog, or a pharmaceutically acceptable salt, derivative, or metabolite thereof, prior to and/or after adopting a ketogenic diet.

Dosages

In some embodiments, the effective amount of the ketamine composition used in the methods of the disclosure is a dose of about 0.01 to about 3 mg of ketamine per kilogram of body weight of the subject being treated (mg/kg), i.e., from about 0.01 mg/kg to about 3 mg/kg body weight. In some embodiments, the effective amount of the ketamine composition used in the methods of the disclosure ranges from about 0.001 to about 3 mg/kg body weight, from about 0.001 to about 2 mg/kg body weight, from about 0.01 mg/kg to about 3 mg/kg body weight, from about 0.01 to about 2 mg/kg of body weight, from about 0.01 to about 1.5 mg/kg of body weight, from about 0.05 to about 1.4 mg/kg of body weight, from about 0.05 to about 1.3 mg/kg of body weight, from about 0.05 to about 1.2 mg/kg of body weight, from about 0.05 to about 1.1 mg/kg of body weight, from about 0.01 to about 1 mg/kg of body weight, or from about 0.05 to about 0.7 mg/kg of body weight. In some embodiments, the dose is about 0.05 to about 0.5 mg/kg. In some embodiments, the dose is less than about 0.5 mg/kg, less that about 0.4 mg/kg, or less than about 0.3 mg/kg body weight. In some embodiments, the effective amount of the ketamine composition used in the methods of the disclosure is a dose in the range of from about 0.01 mg/kg to about 1.5 mg/kg body weight. In some embodiments, the effective amount of the ketamine composition is a dose in the range of from about 0.01 mg/kg to about 1 mg/kg body weight. In some embodiments, the effective amount of the ketamine composition is a dose in the range of from about 0.0.1 mg/kg to about 0.75 mg/kg body weight. In some embodiments, the effective amount of the ketamine composition is a dose in the range of from about 0.75 mg/kg to about 1.5 mg/kg body weight. In some embodiments, the effective amount of the ketamine composition is a dose in the range of from about 0.5 mg/kg to about 1.2 mg/kg body weight. In some embodiments, the effective amount of the ketamine composition is a dose in the range of from about 0.05 mg/kg to about 0.5 mg/kg. In some embodiments, the effective amount of the ketamine composition is a dose of about 0.2 mg/kg or about 0.4 mg/kg body weight. In some embodiments, the dose of the ketamine composition is about 0.01 to about 1 mg/kg, about 0.1 to about 0.5 mg/kg, about 0.8 to about 1.2 mg/kg, about 0.7 to about 1.1 mg/kg, about 0.05 to about 0.7 mg/kg, about 0.01 mg/kg, about 0.05 mg/kg, about 0.1 mg/kg, about 0.2 mg/kg, about 0.3 mg/kg, about. 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, or about 3 mg/kg body weight.

In some embodiments, the dose of the ketamine composition used in the methods of the disclosure per administration is from about 1 to about 250 mg, from about 10 mg to about 300 mg, about 10 mg to about 250 mg, about 10 to about 200 mg, about 15 to about 175 mg, about 20 to about 175 mg, about 8 mg to about 32 mg, about 50 mg to about 75 mg, about 2.5 to about 1.50 mg, about 25 to about 125 mg, about 25 to about 100 mg, about 50 to about 100 mg, about 50 mg to about 75 mg about 75 mg to about 100 mg, or about 75 mg to about 200 mg, about 1 mg, about 2 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, and about 250 mg. In some embodiments, the dose of the ketamine composition is about 50 mg. In some embodiments, the dose of the ketamine composition is about 55 mg. In some embodiments, the dose of the ketamine composition is about 60 mg. In some embodiments, the dose of the ketamine composition is about 65 mg. In some embodiments, the dose of the ketamine composition is about 70 mg. In some embodiments, the dose of the ketamine composition is about 75 mg. In some embodiments, the dose of the ketamine composition is about 80 mg. In some embodiments, the dose of the ketamine composition is about 85 mg. In some embodiments, the dose of the ketamine composition is about 90 mg. In some embodiments, the dose of the ketamine composition is about 95 mg. In some embodiments, the total dose of the ketamine composition is about 100 mg.

In some embodiments, the therapeutically effective amount of the ketamine composition is a sub-anesthetic dose. In some embodiments, the therapeutically effective amount of the ketamine composition is a sub-analgesic dose. In some embodiments, the therapeutically effective amount of the ketamine composition is below the level that results in one or more side effects of ketamine, a ketamine analog, or a pharmaceutically acceptable salt, derivative, or metabolite thereof. In some embodiments, the therapeutically effective amount of the ketamine composition is an anesthetic dose or analgesic dose.

In some embodiments, the (therapeutically) effective amount of the ketamine composition is about 0.01 mg to about 1,000 mg, from about 0.01 mg to about 500 mg, from about 0.1 mg to about 250 mg, or any amount or range therein. In some embodiments, the (therapeutically) effective amount of the ketamine composition is, e.g., about 0.01 mg, about 0.025 mg, about 0.05 mg, about 0.1 mg, about 0.5 mg, about 1 mg, about 5 mg, about 10 mg, about 25 mg, about 50 mg, about 55 mg, about 60 mg, about 65 mg, about 70 mg, about 75 mg, about 80 mg, about 90 mg, about 95 mg, about 100 mg, about 150 mg, about 200 mg, about 250 mg, or about 500 mg.

In some embodiments, a therapeutically effective dose of the ketamine composition may be adjusted depending on conditions of the disease/disorder to be treated or prophetically treated, the age, body weight, general health conditions, sex, and diet of the subject, dose intervals, administration routes, excretion rate, and combinations of drugs.

In some embodiments, the ketamine composition may be administered at a larger initial dose followed by one or more smaller maintenance doses. In some embodiments, the ketamine composition may be administered at a lower initial dose followed by one or more higher doses. Other ranges are possible, depending on the subject's response to the treatment. In some embodiments, the initial dose of the ketamine composition may be the same as, or lower or higher than subsequently administered doses.

The dose may be administered daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In some embodiments, a subject may be administered 1 dose, 2 doses, 3 doses, 4 doses, 5 doses, 6 doses or more of the ketamine composition. In some embodiments, a single dose of the ketamine composition is administered in the present method. In some embodiments, multiple doses of the ketamine composition (e.g., 2 doses, 3 doses, 4 doses, 5 doses, 6 doses, 7 doses, 8 doses, 9 doses, 10 doses or more, including a maintenance dose) are administered in the present method.

In some embodiments, when there are more than one doses of the ketamine composition administered to a subject, the second dose is lower than the first dose. In some embodiments, the second dose is an amount that is at most one-half, one-quarter, or one-tenth the amount of the first dose.

The number and frequency of doses may be determined based on the subject's response to the administration of the composition, e.g., if one or more of the patient's symptoms improve and/or if the subject tolerates administration of the composition without adverse reaction.

In some embodiments, the ketamine composition is administered at least once a day, at least twice a day, at least three times per day, or more. In some embodiments, the ketamine composition is administered at least once a week, at least twice a week, at least three times per week, or more frequently. In some embodiments, the ketamine composition is administered at least twice per month, or at least once per month.

Treatment using the methods of the present disclosure can continue as long as needed.

Dosing Time Frame

The ketamine composition may be administered to a subject in need thereof prior to or after having been on a ketogenic diet. In some embodiments, the ketamine composition is administered to a subject in need thereof prior to having been on a ketogenic diet. In some embodiments, the ketogenic diet is introduced into a treatment regime for treating diseases or disorders other than anorexia nervosa, bulimia and related clinical syndromes, the treatment regime uses a ketamine, a ketamine analog, or a pharmaceutically acceptable salt, derivative, or metabolite thereof, as a nutritional component to improve management of the diseases or disorders. In some embodiments, the ketogenic diet is introduced into in a treatment regime for treating anorexia nervosa and related clinical syndromes, the treatment regime uses a ketamine, a ketamine analog, or a pharmaceutically acceptable salt, derivative, or metabolite thereof, as a nutritional component to improve management of anorexia nervosa and related clinical syndromes. In some embodiments, the ketogenic diet is introduced into a treatment regime for treating bulimia and related clinical syndromes, the treatment regime uses a ketamine, a ketamine analog, or a pharmaceutically acceptable salt, derivative, or metabolite thereof, as a nutritional component to improve management of bulimia and related clinical syndromes.

In some embodiments, the ketamine composition is administered to a subject in need thereof after the subject has been on a ketogenic diet for a period of time. In some embodiments, the ketamine composition is administered to a subject after the subject has been on a ketogenic diet for at least about two weeks. In some embodiments, the ketamine composition is administered to a subject after the subject has been on a ketogenic diet for at least about three weeks. In some embodiments, the ketamine composition is administered to a subject after the subject has been on a ketogenic diet for at least about 1 month. In some embodiments, the ketamine composition is administered to a subject after the subject has been on a ketogenic diet for at least about 2 months. In some embodiments, the ketamine composition is administered to a subject after the subject has been on a ketogenic diet for at least about 3 months. In some embodiments, the ketamine composition is administered to a subject after the subject has been on a ketogenic diet for at least about 4 months. In some embodiments, the ketamine composition is administered to a subject after the subject has been on a ketogenic diet for at least about 5 months. In some embodiments, the ketamine composition is administered to a subject after the subject has been on a ketogenic diet for at least about 6 months. In some embodiments, the ketamine composition is administered to a subject after the subject has been on a ketogenic diet for more than about 6 months.

In some embodiments, the ketamine composition is administered to a subject after the subject has been on a ketogenic diet for a period of time and wherein the subject has a blood ketone level of more than about 0.3 mmol/L of β-hydroxybutyrate. In some embodiments, the ketamine composition is administered to a subject having a blood ketone level from about 0.3 mmol/L to about 3.0 mmol/L of β-hydroxybutyrate. In some embodiments, the ketamine composition is administered to a subject having a blood ketone level from 1.0 mmol/L to about 3.0 mmol/L of 3-hydroxybutyrate. In some embodiments, the ketamine composition is administered to a subject having a blood ketone level from 1.5 mmol/L to about 3.0 mmol/L of β-hydroxybutyrate. In some embodiments, the ketamine composition is administered to a subject having a blood ketone level from 2.0 mmol/L to about 3.0 mmol/L of β-hydroxybutyrate. In some embodiments, the ketamine composition is administered to a subject having a blood ketone level of more than about 3.0 mmol/L of β-hydroxybutyrate.

In some embodiments, the ketamine composition is administered to a subject having a blood ketone level of about 0.6 mmol/L of β-hydroxybutyrate. In some embodiments, the ketamine composition is administered to a subject having a blood ketone level of about 0.7 mmol/L of β-hydroxybutyrate. In some embodiments, the ketamine composition is administered to a subject having a blood ketone level of about 0.8 mmol/L of β-hydroxybutyrate. In some embodiments, the ketamine composition is administered to a subject having a blood ketone level of about 0.9 mmol/L of β-hydroxybutyrate. In some embodiments, the ketamine composition is administered to a subject having a blood ketone level of about 1.0 mmol/L of β-hydroxybutyrate. In some embodiments, the ketamine composition is administered to a subject having a blood ketone level of about 1.1 mmol/L of β-hydroxybutyrate. In some embodiments, the ketamine composition is administered to a subject having a blood ketone level of about 1.2 mmol/L of 3-hydroxybutyrate. In some embodiments, the ketamine composition is administered to a subject having a blood ketone level of about 1.3 mmol/L of β-hydroxybutyrate. In some embodiments, the ketamine composition is administered to a subject having a blood ketone level of about 1.4 mmol/L of β-hydroxybutyrate. In some embodiments, the ketamine composition is administered to a subject having a blood ketone level of about 1.5 mmol/L of β-hydroxybutyrate. In some embodiments, the ketamine composition is administered to a subject having a blood ketone level of about 1.6 mmol/L of β-hydroxybutyrate. In some embodiments, the ketamine composition is administered to a subject having a blood ketone level of about 1.7 mmol/L of β-hydroxybutyrate. In some embodiments, the ketamine composition is administered to a subject having a blood ketone level of about 1.8 mmol/L of β-hydroxybutyrate. In some embodiments, the ketamine composition is administered to a subject having a blood ketone level of about 1.9 mmol/L of 3-hydroxybutyrate. In some embodiments, the ketamine composition is administered to a subject having a blood ketone level of about 2.0 mmol/L of β-hydroxybutyrate. In some embodiments, the ketamine composition is administered to a subject having a blood ketone level of about 2.1 mmol/L of β-hydroxybutyrate. In some embodiments, the ketamine composition is administered to a subject having a blood ketone level of about 2.2 mmol/L of β-hydroxybutyrate. In some embodiments, the ketamine composition is administered to a subject having a blood ketone level of about 2.3 mmol/L of β-hydroxybutyrate. In some embodiments, the ketamine composition is administered to a subject having a blood ketone level of about 2.4 mmol/L of β-hydroxybutyrate. In some embodiments, the ketamine composition is administered to a subject having a blood ketone level of about 2.5 mmol/L of β-hydroxybutyrate. In some embodiments, the ketamine composition is administered to a subject having a blood ketone level of about 2.6 mmol/L of 3-hydroxybutyrate. In some embodiments, the ketamine composition is administered to a subject having a blood ketone level of about 2.7 mmol/L of β-hydroxybutyrate. In some embodiments, the ketamine composition is administered to a subject having a blood ketone level of about 2.8 mmol/L of β-hydroxybutyrate. In some embodiments, the ketamine composition is administered to a subject having a blood ketone level of about 2.9 mmol/L of β-hydroxybutyrate. In some embodiments, the ketamine composition is administered to a subject having a blood ketone level of about 3.0 mmol/L of β-hydroxybutyrate.

Ketone levels may be measured using any methods known in the art and any apparatuses available in the markets. For example, blood ketone levels may be measured using a blood ketone meter. Ketone in urine may be measured, for example, with urine test sticks. Ketone levels may also be measured by measuring breath acetone levels with a portable breath monitor.

In some embodiments, the ketamine composition is administered to a subject after the subject has maintained any of the aforementioned levels of ketone for at least about 5 days. In some embodiments, the ketamine composition is administered to a subject after the subject has maintained any of the aforementioned levels of ketone for at least about 6 days. In some embodiments, the ketamine composition is administered to a subject after the subject has maintained any of the aforementioned levels of ketone for at least about 1 week. In some embodiments, the ketamine composition is administered to a subject after the subject has maintained any of the aforementioned levels of ketone for at least about 10 days. In some embodiments, the ketamine composition is administered to a subject after the subject has maintained any of the aforementioned level of ketone for at least about 2 weeks. In some embodiments, the ketamine composition is administered to a subject after the subject has maintained any of the aforementioned levels of ketone for at least about 3 weeks. In some embodiments, the ketamine composition is administered to a subject after the subject has maintained any of the aforementioned levels of ketone for at least about 1 month. In some embodiments, the ketamine composition is administered to a subject after the subject has maintained any of the aforementioned levels of ketone for at least about 2 months or more.

In some embodiments, the administration of the ketamine composition is continued over a period of up to about 2 days, up to about 3 days, up to about 4 days, up to about 5 days, up to about 6 days, up to about 1 week, up to about 2 weeks, up to about 3 weeks, up to about 4 weeks, up to about 5 weeks, up to about 6 weeks, up to about 7 weeks, up to about 8 weeks, up to about 9 weeks, up to about 10 weeks, or longer.

In some embodiments, the administration of the ketamine composition is administered at least once a week, at least twice a week, at least three times a week, at least once per month, at least twice per month, at least three times per month, or more frequently. Treatment can continue as long as needed.

Methods of Treatment

Described herein are methods of treatment for anorexia nervosa, bulimia and related clinical syndromes in a subject in need thereof, using a combination of ketogenic diet and administration of ketamine or one of its analogs, pharmaceutically acceptable salts, derivatives or metabolites. In some embodiments, the methods comprise placing the subject on a ketogenic diet and maintaining the subject on the ketogenic diet for a period of time sufficient to cause a detectable increase in ketone levels above levels associated without a ketogenic diet, followed by administering an effective amount of a ketamine composition (which is defined as a pharmaceutical composition comprising ketamine, a ketamine analog, or a pharmaceutically acceptable salt, derivative, or metabolite thereof) to the subject, wherein the combination of the ketogenic diet and the administration of the ketamine composition is effective to treat the anorexia nervosa, bulimia and related clinical syndromes in the subject.

In some embodiments the subject is diagnosed with, or is suspected of having anorexia nervosa. In some embodiments, the treatment of the disclosure is administered to an individual based on the judgement of the clinician that the individual has an eating disorder that would benefit from the treatment. Various criteria may also be relied on to identify such individuals and may include reliance on the DSM (Diagnostic & Statistical Manual) which uses BMI as an index for eating disorder severity and classifies anorexia nervosa and BN based on BMI as follows:

Mild BMI>17 kg/m$^2$
Moderate BMI 16-16.99 kg/m$^2$
Severe BMI 15-15.99 kg/m$^2$
Extreme BMI<15 kg/m$^2$ Accordingly, in one embodiment the individual with a history consistent with an eating disorder such as anorexia nervosa has a BMI from about 15 kg/m$^2$ to about 25 kg/m$^2$; in another embodiment the BMI is from about 16 kg/m$^2$ to about 20 kg/m$^2$; in another embodiment the BMI is from about 18 kg/m$^2$ to about 19 kg/m$^2$; in another embodiment the BMI is from about 15 kg/m$^2$ to about 18 kg/m$^2$; and in another embodiment the BMI is from about 15 kg/m$^2$ to about 17 kg/m$^2$; and in another embodiment the BMI is from about 15 kg/m$^2$ to about 16 kg/m$^2$. In some embodiments, the subject has a Body Mass Index (BMI) of less than about 15 kg/m$^2$ and a medical history consistent with anorexia. A medical history consistent with anorexia can include, but not limited to, continuing to be plagued by very disturbing compulsions to exercise excessively, eat in a restricted manner, and have intense negative self-thoughts and anxieties about food, body image, or exercising. In some embodiments, the subject is diagnosed with or suspected of having anorexia nervosa and failed to show significant improvement with usual care, including refeeding, family involvement in refeeding, and personal therapy for about 6 months.

In some embodiments, the subject has maintained a ketogenic diet for at least about 2 weeks and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet for at least about 2 weeks and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet for at least about 2 weeks and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet for at least about 2 weeks and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet for at least about 2 weeks and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet for at least about 2 weeks and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet for at least about 2 weeks and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet for at least about 2 weeks and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet for at least about 2 weeks and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet for at least about 2 weeks and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet for at least about 2 weeks and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet for at least about 2 weeks and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet for at least about 1 month and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet for at least about 1 month and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet for at least about 1 month and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet for at least about 1 month and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet for at least about 1 month and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet for at least about 1 month and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet for at least about 1 month and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet for at least about 1 month and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet for at least about 1 month and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet for at least about 1 month and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet for at least about 1 month and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet for at least about 1 month and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet for at least about 3 months and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet for at least about 3 months and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet for at least about 3 months and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet for at least about 3 months and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet for at least about 3 months and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet for at least about 3 months and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet for at least about 3 months and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet for at least about 3 months and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet for at least about 3 months and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet for at least about 3 months and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet for at least about 3 months and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet for at least about 3 months and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet for a period of time and has a blood ketone level of from about 0.3 mmol/L to about 3.0 mmol/L of β-hydroxybutyrate, and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a blood ketogenic diet for a period of time and has a ketone level of from about 0.3 mmol/L to about 3.0 mmol/L of β-hydroxybutyrate, and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet for a period of time and has a blood ketone level of from about 0.3 mmol/L to about 3.0 mmol/L of 3-hydroxybutyrate, and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a blood ketogenic diet for a period of time and has a ketone level of from about 0.3 mmol/L to about 3.0 mmol/L of β-hydroxybutyrate, and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet for a period of time and has a blood ketone level of from about 0.3 mmol/L to about 3.0 mmol/L of 3-hydroxybutyrate, and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet for a period of time and has a blood ketone level of from about 0.3 mmol/L to about 3.0 mmol/L of β-hydroxybutyrate, and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet for a period of time and has a blood ketone level of from about 1.5 mmol/L to about 3.0 mmol/L of β-hydroxybutyrate, and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet for a period of time and has a blood ketone level of from about 1.5 mmol/L to about 3.0 mmol/L of 3-hydroxybutyrate, and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet for a period of time and has a blood ketone level of from about 1.5 mmol/L to about 3.0 mmol/L of β-hydroxybutyrate, and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet for a period of time and has a blood ketone level of from about 1.5 mmol/L to about 3.0 mmol/L of 3-hydroxybutyrate, and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet for a period of time and has a blood ketone level of from about 1.5 mmol/L to about 3.0 mmol/L of β-hydroxybutyrate, and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet which restricts meals taken by the subject to comprise fats and proteins/carbohydrates in a ratio of about 3:1 by weight, and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet which restricts meals taken by the subject to comprise fats and proteins/carbohydrates in a ratio of about 3:1 by weight, and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 3:1 by weight, and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet which restricts meals taken by the subject to comprise fats and proteins/carbohydrates in a ratio of about 2:1 by weight, and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet which restricts meals taken by the subject to comprise fats and proteins/carbohydrates in a ratio of about 2:1 by weight, and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 2:1 by weight, and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

In some embodiments, the subject has maintained a ketogenic diet which restricts meals taken by the subject to comprise fats and proteins/carbohydrates in a ratio of about 1:1 by weight, and thereafter, is administered one or more doses of a ketamine composition comprising esketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered one or more doses of a ketamine composition comprising esketamine by infusion, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered one or more doses of a ketamine composition comprising arketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered one or more doses of a ketamine composition comprising arketamine by infusion, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered one or more doses of a ketamine composition comprising a racemic mixture of esketamine and arketamine by infusion, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered one or more doses of a ketamine composition comprising a racemic mixture of esketamine and arketamine by infusion, each dose comprising from about 0.75 mg/kg to about 1.5 mg/kg body weight of the ketamine composition.

In some embodiments, the subject has maintained a ketogenic diet which restricts meals taken by the subject to comprise fats and proteins/carbohydrates in a ratio of about 1:1 by weight, and thereafter, is administered intranasally one or more doses of a ketamine composition comprising esketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered intranasally one or more doses of a ketamine composition comprising esketamine, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered intranasally one or more doses of a ketamine composition comprising arketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered intranasally one or more doses of a ketamine composition comprising arketamine, each dose comprising from about 0.75 mg/kg to about 1.5 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered intranasally one or more doses of a ketamine composition comprising a racemic mixture of esketamine and arketamine, each dose comprising from about 0.01 mg/kg to about 3 mg/kg body weight of the ketamine composition. In some embodiments, the subject has maintained a ketogenic diet which restricts meals taken by the subject to comprise fats and proteins/carbohydrates in a ratio of about 1:1 by weight, and thereafter, is administered intranasally one or more doses of a ketamine composition comprising a racemic mixture of esketamine and arketamine, each dose comprising from about 0.75 mg/kg to about 1.5 mg/kg body weight of the ketamine composition.

This present disclosure will be better understood from the Examples, which follow. However one skilled in the art will readily appreciate that the specific methods and results discussed are merely illustrative of the disclosure as described more fully in the claims that follow thereafter.

EXAMPLES

Example 1. Case Study

Severe and enduring anorexia nervosa, or chronic anorexia nervosa, in adults is an intractable and debilitating disorder, with very low rates of response, and rare remission and restoration of functioning (Hay et al., 2012). There is no approved treatment. Severe and enduring anorexia nervosa in adults is usually defined as symptoms persisting for at least 3 years despite treatment involving at least 2 modalities, such as different forms of therapy (Touyz et al., 2015).

A 29-year-old patient presented with a 15-year history of chronic anorexia nervosa with restricted eating, obsessive exercise, and co-morbid alcoholism and drug addiction. These had started with dietary restrictions with the aim of "eating healthier" at age 14, but soon became obsessive-compulsive. At the end of the freshman year, the patient's weight was 136 pounds (61.7 Kg) and the height was 5 feet 5 inches (165.1 cm), thus calculated to a Body Mass Index (BMI) of 22.6.

Eighteen months later, the subject had a grand mal seizure, her weight was 89 pounds (40.4 Kg; BMI 14.8) and she was hospitalized for 6 weeks. The subject was partially weight restored to 109-120 pounds (54.4 Kg; BMI 18.1) and discharged for outpatient treatment. Efforts to enforce family based treatment were largely unsuccessful, as she was resistant. She maintained her weight, but continued to suffer personality changes.

Over the ensuing years, the subject developed a dependency on alcohol, abused cocaine, and briefly snorted heroin. She had several stints in alcohol & drug rehabilitation programs. In spite of these difficulties, the subject graduated from university, worked for several years as a recovery coach in a wilderness rehabilitation program, and began graduate school. The subject continued to eat in an idiosyncratic manner—often only candy and chocolate ice cream for days, and she continued to exercise compulsively and excessively. According to the subject's own description, there was an "AN voice" inside of her constantly telling her that "sugar and carbs are good food fat people eat, not for AN people, so since you are so good eating all this sugar, you can consider yourself healthy."

The only medications the subject was prescribed were lamotrigine for six months following the seizure, and 70 mg/day of Vyvanse, which she was prescribed for one year. She has been in outpatient supportive psychotherapy intermittently for most of these years, and her weight has varied between 116 (52.6 Kg; BMI 19.3) and 128 (58.1 Kg; BMI 21.3) pounds. The higher weights were during times of active drug use.

At the age of 29, after sustaining sobriety from drugs and alcohol for 15 months, and continuing to be tormented by anorexic behaviors and intrusive thoughts, she began to orchestrate her own recovery by first adopting a ketogenic diet. The aim of this diet was to induce nutritional ketosis and avoid the ketosis of starvation. The subject learned from an experienced ketogenic diet medical nutritionist how to prepare high fat, low carbohydrate meals and smoothies heavy with oil. She eliminated non-nutritive sweeteners, which she used almost on everything she ate prior to adopting the ketogenic diet. The ketogenic diet the subject adopted is a modified range ketogenic diet based on a ratio of (fat in grams) to (protein+carbohydrates in grams) of between 1:1 and 2:1. She measured breath acetone levels with a portable breath monitor, approximately 4-5 times/week on average, and found her ketone level was around the "medium range" while on the ketogenic diet.

After 3 months on the ketogenic diet, when she was in moderate ketosis for 14 days based on portable breath monitor reading, she started with intravenous (IV) ketamine treatment. After a comprehensive evaluation, she was given a 40-minute infusion of racemic IV ketamine at dose of 0.75 mg/kg (42.68 mg), in 30 cc 0.9% Normal Saline. Within one hour, she felt the AN voice was weakening and she had more ability to "be herself." She then had three more infusions over the next fourteen days at doses 1.0 mg/kg, 1.1 mg/kg, and 1.2 mg/kg. By the end of treatment, she no longer felt anorexic any more. She could exercise and stop exercising at her own wish. Her weight has maintained at about 125 pounds (56.7 Kg; BMI 20.8) throughout the treatment (duration 15 days) and even months after her treatment.

Example 2. Clinical Study

Based on the case study described in Example 1, a modified ketogenic diet and ketamine infusions are synergistic in treating severe and enduring anorexia nervosa (SE-AN or chronic anorexia). An outpatient clinical study is developed to document the clinical characteristics, responses, side effects and clinical course of this sequenced treatment using a modified ketogenic diet and ketamine for chronic anorexia nervosa. The study uses an open-label clinical trial design. Results will optimize low-dose ketamine clinical development.

Study Site

The modified ketogenic diet phase (Part I) of the sequenced procedure will begin at a local facility, with a large kitchen. The facility will be reserved exclusively for program participants, support partners, and study staff during the Part I 2-day program.

Recruitment

The clinical trial is for medically stable adults with SE-AN who have failed to respond to at least 2 different treatments for 3 years or more, and who continue to suffer anorexic thoughts and compulsions. The inclusion criteria and exclusion criteria for a patient's eligibility to participate in the study are as follows.

Inclusion Criteria:
- Adults between 18 and 65
- Anorexia nervosa diagnosis for at least 3 years
- Treatment resistance, as evidenced by having adequate trials and failures of at least 2 treatments for anorexia nervosa
- Body Mass Index (BMI)≥18.5 kg/m$^2$ (this is a measure of weight and height, and in general normal is considered between 18.5 and 24.9 kg/m$^2$)
- Stable weight for the last 3 months (no consistent change greater than 5 lbs. (2.3 kg))
- Abstinence from substance abuse for at least 3 months, including abstinence from cannabis use
- Currently under the care of a primary care provider (PCP)
- Participant must agree to have PCP contacted by study staff
- Willingness to participate in person in a 2-day program for education and adoption of a modified ketogenic diet
- Identified support partner who will attend the 2-day program with participant
- Willingness to have weight recorded and reported by either the PCP or participant support partner according to the following schedule:
  - Daily for 1 week following the 2-day program
  - Weekly for 1 month during At Home Diet Maintenance
  - At 1, 3, 6, 9 and 12 months following the final ketamine infusion
- Willingness to participate in safety and efficacy monitoring of modified diet by study staff
- Willingness to attend between 4 and 6 clinic visits for administration of parenteral racemic ketamine, the study medication
- Willingness to be contacted for scheduled follow-up for 12 months following study medication
- Willingness to agree not to post any of the participant's personal medical data related to the study or information related to the study on any website or social media site (e.g., Facebook, Twitter, Instagram) until they have been notified that the study is completed Exclusion Criteria:
- Concomitant disease (e.g., gastrointestinal, renal, hepatic, endocrine, respiratory, or cardiovascular) or condition or any clinically significant finding at screening that could interfere with the conduct of the study or that would pose an unacceptable risk to the participant in this study
- Clinically significant lab abnormalities or vital signs at the time of screening (e.g., ALA or AST>2.5 times upper limit or normal; total bilirubin or creatinine >1.5 upper limit of normal) (re-testing of safety screening labs is allowed)
- Primary carnitine deficiency, carnitine palmitoyl transferase I or II deficiency, or carnitine translocase deficiency
- β-oxidation defects, acyl-CoA dehydrogenase deficiencies, pyruvate carboxylase deficiency
- Porphyria
- Concurrent treatment with carbonic anhydrase inhibitors (i.e., topiramate, zonisamide)
- Bulimia nervosa as the primary diagnosis
- Weight change of >5 lbs. (2.3 kg) in last 3 months
- Pregnancy
- Sexually active females who are not using birth control
- Interstitial cystitis
- Unmanaged/unstable hypertension (SBP>140 mm Hg or diastolic BP>90 mm Hg)
- Unstable cardiac arrhythmia
- Uncontrolled seizure disorder or seizure within 30 days before screening
- QTc interval of 470 milliseconds or greater
- Current or past history of psychotic disorder
- Active suicidal ideation or considered by the investigator to be at high risk for suicide
- Enrolled in any clinical trial or used any investigational agent, device and/or investigational procedure within the 30 days before screening, or does so concurrently with this study Screening Evaluation by the Investigator Adults who are between 18 and 65 years old with SE-AN, with a history of a diagnosis of severe anorexia nervosa for 3 or more years with persistent anorexic thoughts and behaviors despite 2 previous treatments, are eligible for further screening.

Recent medical, psychiatric, and psychotherapy records are requested for all participants from their treating providers (PCP, psychiatrist/advance practice registered nurse (APRN), and therapist) before consultation with the investigator and reviewed when provided/available. Procedures for obtaining medical records from treating providers will be HIPAA compliant, and written informed consent allowing records to be shared with the investigator will be obtained from participants.

During the investigator consultation, extensive psychiatric history are obtained, including history of onset of eating disorder; cognitive, behavioral and affective eating disorder symptoms; weight history and BMI; nutrition history, laxative use, food allergies, intolerances, and preferences; psychotherapy; outpatient, residential and inpatient treatments; and social and family history.

All diagnoses are made during consultation using The Diagnostic and Statistical Manual of Mental Disorders (DSM-5) criteria. The diagnosis of anorexia nervosa are confirmed with Eating Disorder Assessment of DSM-5 Feeding and Eating Disorders (EDA-5) Version 3.0 (Adult). Depressive symptoms are assessed by administering the Patient Health Questionnaire-9 (PHQ-9), a widely-used brief scale which grades the severity of depressive symptoms.

The participant's history of co-morbid psychiatric symptoms, past medication trials, history of previous suicidal ideation and attempts, and clinical assessment of suicide risk factors are obtained and reviewed. Medical and surgical history are obtained. Detailed history of substance use/misuse are also obtained.

Determination of eligibility for participation in this clinical trial are made by the investigator in consultation with a relevantly experienced registered dietitian nutritionist. The emphasis in determining eligibility is on ensuring safety, by eliminating participants who are physically or psychiatrically unstable.

The participants for this study are a group of adults with SE-AN and body mass index (BMI) within normal limits (although often on low end), yet who continue to be plagued by very disturbing compulsions to exercise excessively, eat in a restricted manner, and have intense negative self-thoughts and anxieties about food, body image, or exercising.

If upon initial screening a participant is considered an appropriate candidate for this clinical trial, she/he will undergo further screening with the following tests:

Urine toxicology screen
Electrocardiogram (ECG) to ensure QTc interval is not ≥470 milliseconds
Complete blood count
Electrolytes, glucose, magnesium, calcium, phosphorus, blood urea nitrogen/creatinine
Pre-albumin
12-hour fasting lipid profile
Serum acylcarnitine
Liver function tests, specifically AST, ALT, alkaline phosphatase
Urinalysis
Serum pregnancy test (females)

All female participants will be screened twice for pregnancy using a serum pregnancy test: (1) during study screening as above, and (2) before beginning ketamine infusions described below.

Except for serum pregnancy tests, the investigator will review lab tests provided by the PCP within the past month in lieu of ordering them again, and ECG results obtained within the past 3 months.

Participants who are prescribed psychiatric medications will have those managed by the prescriber throughout the entire study and follow-up period.

Participants who are engaged in individual, group, and/or family psychotherapy may continue to see their therapist(s) throughout both Part I and Part II of this sequenced procedure, and during the 12-month follow-up period.

Informed Consent

For participants determined to be candidates for this study, the research associate, registered dietitian nutritionist and investigator reviews the risks, benefits and alternatives to this study with the patient in detail. The possible side effects of the modified ketogenic diet proposed in this study will be explained, including transient low blood glucose, dehydration, fatigue, muscle cramping, gastrointestinal symptoms and unintended weight loss, as well as the clinical signs and symptoms of "keto flu" which sometimes occurs when beginning the diet. The importance of beginning the study in person by participating in a 2-day educational and experiential program to learn how to initiate the diet safely in anorexia nervosa, and the importance of participating in daily monitoring via Zoom/phone for the first week after returning home, and weekly during the remainder of Part 1 are emphasized. The requirement to have body weight independently measured and recorded by the support partner, or PCP on schedule, is emphasized.

The investigator explains the specific risks of off-label intravenous ketamine infusions with racemic ketamine at sub-anesthetic doses, which is increasingly used in the treatment of several psychiatric disorders where other treatments have failed, the potential side effects of subanesthetic ketamine infusions, the safety precautions in place in the clinic for ketamine administration, the recommendations for aftercare, and the requirement for collaboration with the participant's PCP.

This conversation takes 30-60 minutes, with time permitted for an extended discussion, for the patient to ask questions, to discuss their potential participation with their identified support partner, and to make a decision about whether or not to proceed with this clinical trial, without coercion.

The participant's freedom to withdraw from the study, i.e., to decide to not begin, to discontinue the study, or to change one's mind about participation in the study at any time is reviewed in detail and outlined in the Informed Consent document.

All participants who wish to proceed provide written informed consent to participate in this clinical trial using the Informed Consent document. All signatures are obtained and witnessed to obtain informed consent. All participants who provide written informed consent are evaluated by the investigator regarding their competence to provide informed consent as evidenced by their demonstrated ability to understand, ask questions, make a determined decision, and explain their reasoning.

Detailed Description of Sequenced Procedure
Part I: Modified Ketogenic Diet
A. Immersive 2-Day Instructional Program Part I consists of a reframing of the disorder of anorexia nervosa as a metabolic disorder, and introduction to the idea that a modified ketogenic diet might address the core metabolic issue that perpetuates the disturbing anorexic behaviors, obsessions, and compulsions. The training on the metabolic theory and the mechanics of adopting the diet take place at a facility close to the investigator's outpatient clinic. Each participant must be accompanied by a support partner (adult family member or friend) throughout the duration of the 2-day program.

The use of a restrictive diet, such as the modified ketogenic diet, is a dramatic departure from the current treatment paradigm employed at most anorexia nervosa treatment centers where it is stressed that "all foods are good foods." Since it is anticipated that all participants have been exposed to this paradigm, it is believed that participants and their support partners would benefit from an intensive opportunity in person, and with group support from other participants and their support partners, for instruction, support, meal-planning and preparation, and cognitive restructuring.

The registered dietitian nutritionist on the research team, an international expert in ketogenic diets for neurologic conditions, will lead the 2-day program and introduction to the modified ketogenic diet (Kossoff, Zupec-Kania, et al., 2018). The investigator will be available to review medical and psychiatric concerns.

The research associate will introduce participants and their support partners to the view that anorexia nervosa can be re-conceptualized as primarily a metabolic disorder. The research associate reviews the Adaptation to Flee Famine theory (Guisinger, 2003) and presents evidence that a modified ketogenic diet can address the sense of famine, allow individuals with SE-AN to separate themselves from the disorder, and attain emotional freedom from the "inner anorexic voice" that holds them hostage.

Topics covered during the 2-day program may include:
Metabolic basis for a modified ketogenic diet
Method of monitoring ketones using testing of blood, urine or exhaled air—participants are given an acetone breath monitor, instructed in its use, link the accompanying App to the study, and take these monitors home with them for twice daily use (a.m. and p.m.)
How to graduate into high-fat, low-carb-meals and snacks with easy to digest foods Avoid talking about calories, but talk about adequate fat in diet Prepare and taste modified ketogenic meals, smoothies and high-fat foods Learn about importance of supplements—participants are given a twice daily multivitamin during the program and a 1 month supply to take home Check for low blood sugar and learn how to avoid, recognize and treat transient low blood sugar Stress the importance of hydration Explain the "keto flu" which is marked by low grade malaise as the body adapts to a ketogenic diet, and how to avoid or ameliorate it Discuss the difference between starvation ketosis and nutritional ketosis, and stress how the study is aiming for the latter—it is anticipated that all participants have probably experienced starvation ketosis during their struggle with anorexia nervosa Address the necessity of objective weight monitoring for participants in this trial to ensure safety, and minimize the risk of weight loss on a modified ketogenic diet. The issues of being weighed, and whether patients with anorexia nervosa should know their weight, or be blinded, is an active area of debate (Froreich et al., 2020). Some patients feel it is empowering to know their weight, while others feel it makes recovery more difficult. The study will allow participants to decide for themselves if they want to know their body weight, but will insist that the participant's weight be measured, recorded, and reported by a trusted third party—either their PCP or their support partner. Each participant is given her/his own individual scale used at the 2-day program to minimize differences between scales. The research associate contacts the designated weigher on the following schedule during At Home Diet Maintenance to obtain recorded body weight:

Week 1: Daily

Weekly at Weeks 2, 3, 4 (and up to Week 8, if extended)

Stress that, although meticulous weight checks are necessary to ensure participants' safety in this trial, in general participants should not focus on weight—how the modified ketogenic diet calls for much smaller food portions than a nonrestrictive diet, which might make eating meals easier, is discussed Stress importance of low impact exercise like yoga or massage to ease transition to ketogenic diet Review necessity of feedback during At Home Diet Maintenance Following the program, all participants will be invited to participate in an optional weekly support meeting with study staff during At Home Diet Maintenance.

Adverse Events

Adverse Events (AEs) are assessed each day by general inquiry, observation, daily weight obtained by research associate, and daily ketone measurements. Frequent AEs include weight loss, constipation, "keto flu" lethargy and muscle cramping at initiation. Less frequent AEs include hypoglycemia, nausea, vomiting and kidney stones. Blood sugar finger sticks are obtained for symptoms of hypoglycemia. Cardiac arrhythmia is a very rare complication, only reported in classic ketogenic diet initiation, and not in the modified ketogenic diet used in this study.

B. At Home Diet Maintenance

Participants return home and adopt and adapt to the modified ketogenic diet with monitoring for safety and efficacy as follows:

Week 1: Daily call/Zoom meeting by research associate to each participant. The research associate answers questions, offer support, and assess for AEs. The call is recorded and transcribed for later qualitative analysis. If any concerns or AEs arise, the research associate immediately notifies the investigator.

Week 2, 3, 4: Weekly call/Zoom meetings by research associate to each participant. The research associate answers questions, offer support, and assess for AEs. The call is recorded and transcribed for later qualitative analysis. If any concerns or AEs arise, the research associate immediately notifies the investigator. Weekly meetings continue up to 8 weeks, if extended.

The research associate contacts the support partner or PCP to obtain objectively recorded body weight for each participant or according to the following schedule:

Week 1: Daily

Week 2, 3, 4: Once a week (up to 8 weeks, if extended)

If the participant has lost weight of >2 lbs (0.9 kg), the investigator is notified and an objective weight measurement is obtained the following day. If the weight loss is valid, the investigator discusses the issue with the participant, the PCP, the support partner if necessary. The investigator decides whether the participant is given an opportunity to regain the weight in a very short time frame in order to remain in the study, or withdrawn from the study.

Daily availability throughout At Home Diet Maintenance of the investigator, registered dietitian nutritionist, and research associate if a participant or support partner has questions or concerns about the modified ketogenic diet or reports an adverse event (AE).

At the end of 4 weeks, the investigator, in consultation with the registered dietitian nutritionist and research associate, decide if the participant is eligible to advance to Part II Intravenous Ketamine Infusions or requires more time to adapt to the modified ketogenic diet, up to an additional 4 weeks.

A participant who is unable to participate in or demonstrate adherence to the modified ketogenic diet, or who experiences a serious AE, is not eligible to proceed to Part II Intravenous Ketamine Infusions.

Participants are informed that there is no data regarding the length of time to remain on a modified ketogenic diet for it to be effective in its relationship to treating symptoms of SE-AN. In this study, a 4-8 week period is used to "prime" the body's response to ketamine and continued use throughout the study and follow-up period is recommended. However, after Part II Intravenous Ketamine Infusions is completed, it is recognized that diet liberalization is an individual decision.

Adverse Events (AEs)

Medical concerns and AEs related to adaptation to the modified ketogenic diet are reviewed with the investigator, and addressed as needed with the participant's PCP.

If a participant experiences significant weight loss as an AE ($\geq 2$ lbs (0.9 kg) on two consecutive days), the investigator discusses the issue with the participant, notifies the PCP, and decides whether the participant is to be given an opportunity to regain the weight in a very short time frame in order to remain in the study, or will be withdrawn from the study.

Part II: Intravenous Ketamine Infusions

Participant Preparation. Participants are instructed to have no food for 4 hours before each clinic visit for intravenous ketamine infusions.

Participants are weighed at the clinic before each ketamine infusion, and recline comfortably in quiet, private rooms on leather chairs with optional gel heating, dimmed lighting and the option of listening to their own soft music with eye shades. All participants are discouraged from use of visual stimuli, texting, or cell phone use during the infusion.

Dosing and Administration of Ketamine. Racemic ketamine (50 mg/ml) is obtained from a variety of manufacturers. Racemic ketamine is commercially available and FDA approved as an anesthetic for adults in the proposed age range, and has been safely used around the world for the past 50 years intravenously at doses 2.5-5 times higher than the doses used in this study, and for periods lasting up to 15 times longer than the infusion duration in this study; in some clinical programs for headache, racemic ketamine infusions have been administered continuously for up to 72 hours.

Ketamine is stored according to Drug Enforcement Administration (DEA) regulations, dispensed by the investigator, and administered by research registered nurses (RNs) at the clinic.

An indwelling catheter is placed in the ideal vein, and pulse, blood pressure, pulse-oximetry and continuous cardiac waveform (CareTaker Medical Monitoring) are obtained for continuous monitoring.

The first ketamine infusion begins as a single infusion with a proposed dose of 0.75 mg/kg. Dosing is based on data derived from previous pre-clinical and clinical studies in adults, research reports, and clinical practice among the American Society of Ketamine Physicians, Psychotherapists and Practitioners (ASKP3), as well as the experience of the investigators. Subsequent infusions follow a serial titrated dosing paradigm according to participants' weight (Calabrese, 2019).

This is identical to the first dose of intravenous racemic ketamine administered to the patient with SE-AN in the case study described in Example 1.

The investigator may lower the initial ketamine dose for a participant to as low as 0.3 mg/kg if clinically indicated. The initial ketamine dose may be increased during the first infusion in increments of 0.1 mg/kg after 15 minutes if there is no evidence of end-gaze nystagmus, a decrease in verbal fluency, and dissociation by patient self-report and observation, and again after another 15 minutes if none of these are still present, to a maximum of 0.95 mg/kg.

The calculated dose of ketamine for each infusion is diluted to 20 ml with 0.9% NS and administered intravenously at a constant rate over 45 minutes using a MedFusion 3500 syringe pump. Participants without venous access are offered their calculated dose as an intramuscular injection into the deltoid.

Active monitoring throughout the infusion and for 30 minutes thereafter ensures safety and tolerability. Tolerability is assessed by the investigator throughout each infusion and throughout the study.

If tolerability concerns arise during an infusion, the investigator may adjust the infusion rate, reduce the dose, or discontinue the infusion based on the assessment of tolerability, Adverse Events (AEs), or due to medical necessity. If clinically significant agitation occurs, the investigator may administer midazolam 1-2 mg IV×1 dose. AEs are assessed at every clinic visit.

Discharge instructions are reviewed by study staff, and discharge criteria (see below) are met by the participant before discharge from the clinic.

Following the first ketamine infusion, participants are administered a short series of up to 6 infusions of racemic ketamine scheduled over 2-3 weeks, with infusion intervals of 1-5 days. Rarely, due to travel logistics, infusions may be administered on consecutive days.

During subsequent infusions, the dose of racemic ketamine may be held at the starting dose or titrated to achieve and maintain dissociation. Dissociation has been reported to be associated with response and remission of other psychiatric conditions to ketamine infusions, such as treatment-resistant depression and suicidal ideation (Calabrese, 2019).

Dose titration for each subsequent infusion for participants is in increments of 0.1-0.25 mg/kg and is based upon physiologic and emotional tolerability of the prior infusion, participant self-report of improvement in target anorexia symptoms, decrease in PHQ-9, and improvement in cognitive and subjective symptoms of anorexia, to a maximum of 1.5 mg/kg. Infusion duration may be increased up to 60 minutes if dissociative symptoms during any infusion are reported as too intense.

The dose titration schedule for each participant are determined by the investigator, who has had extensive clinical experience over the past 5 years personally administering off-label racemic ketamine infusions to patients with treatment-resistant depression and several other psychiatric conditions.

Continuous Monitoring. All participants are continuously monitored throughout each infusion for P, BP, R, 02% sat and cardiac waveform using Caretaker Medical Monitoring, with continuous recording, wireless remote observation, and repeated nursing assessments during and after each infusion. A written record of the entire infusion parameters is maintained for the participants. In some instances, if the Caretaker device is not available, the infusion RN obtains repeat assessments of vital signs before, during and after the infusion.

To meet criteria for discharge from the clinic visit, participants are fully awake and alert with mental status returning to pre-infusion baseline and have at least 2 consecutive vital signs that are within 20% of baseline.

Adverse Events (AEs). Adverse events (AEs) or side effects to ketamine infusion are assessed by open-ended general inquiry, observation, and continuous monitoring in the clinic.

Ketamine is a sedative/analgesic agent and general anesthetic for human use and has a favorable acute safety profile. Over the past several decades, ketamine has been administered to several million adults and children at doses 2.5 to 5 times higher than the doses proposed here and for much longer infusion durations. It may produce mild to moderate increases in blood pressure, heart rate, and cardiac output due to its sympathomimetic effects. Other potential side effects include sedation, headache, nausea, dizziness, and restlessness. Because ketamine is administered intravenously, there is a risk of pain and irritation at the IV site. The risks of IV placement include pain, bruising, and the slight possibility of infection at the site.

Participants with a history of easy nausea, GI distress or vestibular dysfunction will be offered ondansetron 4-8 mg IVP or ondansetron ODT 4-8 mg SL before each infusion. Side effects of nausea are managed with additional ondansetron 4 mg IVP during or after the infusion, or dimenhydrinate 25-50 mg after the infusion. Metoclopramide 5 mg IVP or IM is available for prn use for severe nausea before, during and immediately following infusion.

The reported incidence of ketamine-induced perceptual disturbances varies from less than 5% to greater than 30% and may manifest as vivid dreaming, visualization of psychedelic color, suspension in space, kaleidoscopic floating, and out-of-body experiences referred to as dissociation.

Some patients describe these experiences as pleasurable, joyful, and fascinating, while others find them bizarre or frightening. Carpenter (1999) systematically collected short-term outcome and potential patient distress data during ketamine challenge interviews from three North American institutions. These studies suggest that dissociative symptoms are transient, usually lasting less than 60 minutes and rarely longer than 2 hours.

In this clinical trial, dissociation is anticipated and is framed as a desirable indicator of potential efficacy and response rather than as an adverse event. Participants are carefully prepared to expect it with examples of dissociative symptoms before parenteral administration begins. Rare side effects of extreme anxiety or fear are managed by the investigator by pausing or slowing the infusion, administering midazolam 1-2 mg slow IVP, or by stopping the infusion.

Risks of midazolam include sedation and respiratory depression. Midazolam has a very rapid onset of action and short half-life (t½=2.5 hours). It is used quite commonly in low doses in psychiatry, anesthesia, and emergency settings when ketamine produced restlessness or agitation.

Morgan et al. (2004) found that an 80-minute infusion of either 0.4 or 0.8 mg/kg ketamine in healthy volunteers does not result in any residual effects 3 days later. Lahti et al. (2001) reported no adverse events of up to 4 doses of 0.1-0.5 mg/kg IV ketamine given over a period of 2 weeks, at the 8-month follow-up. Mills et al. (1998) reported that side effects of 10-hour infusions of 20 mg/hour ketamine (headache, nausea, sedation, revival of distant memories) in patients with eating disorders no longer occurred after the first infusion or were no longer seen as unpleasant. Goldberg et al. (2005) reported that side effects of 10 4-hour infusions of up to 20 mg/hour of ketamine were minimal with only 7-13% experiencing restlessness, headaches, or significant heart rate increases. Feifel et al. (2020) reported only 0.7% of 6630 patients treated with six or more repeated parenteral ketamine infusions for depression experienced a side effect that led to discontinuation of treatment. Chronic high-dose ketamine abuse has been reportedly associated with structural and functional brain changes, associated cognitive problems, and bladder inflammation.

There is no safety data regarding ketamine during pregnancy, so pregnant participants will be excluded from this study. Participants should not become pregnant or father a baby while in this research study. If a participant becomes pregnant during this study, this research may hurt the fetus in ways that are unknown. The unknown risks may be minor or major (death).

All participants are encouraged to maintain regular contact with their PCP throughout the study, including during the short series of ketamine infusions, and will be provided with daytime and emergency contact numbers for the study staff and investigator.

Clinical Outcome Measures

Clinical outcomes are assessed qualitatively and quantitatively. Every Zoom/phone meeting is recorded, transcribed and subject to qualitative analysis. The focus is on participants' experience of the diet and changes in their symptoms of anorexia. Quantitative analysis includes measures of body weight, breath ketones, 24-hour food recall interview, and validated questionnaires addressing food preferences, core symptoms of anorexia nervosa and depression, and functional restoration and recovery in anorexia nervosa.

The Geiselman Food Preference Questionnaire (FPQ) is used to assess the preference for a variety of foods at the beginning of the Immersive 2-Day Instructional Program and at the end of the At Home Diet Maintenance Period, to assess whether the tolerability and preference for fats change with adaptation to the modified ketogenic diet. Geiselman Food Preference Questionnaire (FPQ), a validated questionnaire that assesses preference for a variety of foods, including fats, on a 9-point Likert scale with higher scores indicating higher preference. The FPQ is related to objective measures of energy and fat intake in patients with anorexia nervosa as well as in healthy individuals (Schebendach et al., 2019).

A brief 24-Hour Dietary Recall interview is conducted by the research associate to assess adaptation to the modified ketogenic diet. (Thompson et al., 2015)

The following three self-administered questionnaires are used to assess change in symptoms of anorexia nervosa. All three questionnaires are constructed to be administered at time intervals of one month or greater:

Eating Disorder Examination Questionnaire (EDE-Q), a 28-item self-administered scale that assesses the range severity of eating disorder symptoms across the domains of dietary restraint, eating concern, weight concern, and shape concern (Fairburn, 1994).

Eating Disorder Recovery Endorsement Questionnaire (EDREQ), a 28-item self-administered rating scale that measures severity of eating disorder symptoms across 4 domains: dietary restraint, eating concern, weight concern, and shape concern. Global score and sub-scores range from 0-6 with higher scores indicating higher severity (Bachner-Melman et al., 2018).

Clinical Impairment Assessment (CIA) for Eating Disorders, a 16-item self-administered rating scale which measures severity of psychosocial impairment in domains of life typically affected by eating disorders (Fairburn, 1994).

The Patient Health Questionnaire (PHQ-9) is used to assess change in symptoms of depression. PHQ-9 is a well-studied 9-item self-administered rating scale that measures severity of depressive symptoms (Kroenke, et al., 2010).

Schedule of Outcome Assessments

Clinical outcome measures are assessed at key points during the study and follow-up period.

Body Weight is objectively recorded by PCP or support partner and obtained by the research associate as follows:
At Home Diet Maintenance: Daily during Week 1
At Home Diet Maintenance: Week 2, 3, 4
After final ketamine infusion: Month 1, 2, 3, 6, 9, 12
Notably, body weight is obtained during Part II Ketamine Infusions at the clinic before each ketamine infusion.

Ketone levels is recorded by participant via breath acetone according to the following schedule:
Immersive 2-Day Instructional Program: Daily in the a.m. and p.m.
At Home Diet Maintenance: Every other day in the a.m. and pm
Ketamine Infusions: Weekly
After final ketamine infusion: Month 1, 2, 3, 6, 9, 12

Brief 24-Hour Food Recall is obtained by the research associate or dietitian/nutritionist during scheduled Zoom/phone meetings as follows:
Immersive 2-Day Instructional Program: Day 1
At Home Diet Maintenance: Daily during Week 1
At Home Diet Maintenance: Week 2, 3, 4
After final ketamine infusion: Month 1, 2, 3, 6, 9, 12

The Geiselman FPQ is administered as follows:
Immersive 2-Day Instructional Program: Day 1
At-Home Diet Maintenance period: Week 4 or at the end of this period, if extended The EDE-Q, EDREQ and CIA is administered as follows:
Immersive 2-Day Instructional Program: Day 1
At Home Diet Maintenance: Week 4 (and if extended to 8 weeks: Week 8)
After final ketamine infusion: Day 1 and Month 1, 2, 3, 6, 9, 12

The PHQ-9 is administered as follows:
Immersive 2-Day Instructional Program: Day 1
At-Home Diet Maintenance: Week 2, 4
Ketamine Infusion: Immediately preceding each infusion, in keeping with current standards of clinical practice in the community to reflect symptoms since last infusion
After final ketamine infusion: Month 1, 2, 3, 6, 9, 12

Qualitative interviews are conducted as follows:
Each interview is recorded and transcribed. The interviewer is the research associate, dietitian nutritionist, or investigator. Participants are asked to describe how he/she is feeling, behaving, coping, eating, etc. Participants are asked how they think the treatment affected them. These response are recorded, transcribed, and subject to qualitative analysis.
At Home Diet Maintenance: Daily during Week 1
At Home Diet Maintenance: Weekly during Weeks 2, 3, 4, and up to 8
After final ketamine infusion:
  Daily during Week 1
  Weeks 2, 3, 4
  Month 1, 2, 3, 6, 9, 12.

These interviews include the following additional queries:
Interim history of new-onset medical problems, changes in medication, therapies, interim history of psychiatric or eating disorder hospitalizations or programs
Interim history of substance misuse, including self-administration of ketamine or hallucinogens
Interim history of additional ketamine treatment or ketamine-assisted psychotherapy All participants are invited to participate in an optional weekly group support meeting with study staff during At Home Diet Maintenance, and an optional monthly group support meeting with study staff during the 12-month follow-up period.

Assessment of Safety

All participants are evaluated for safety and tolerability during screening and throughout the trial. During screening, this safety and tolerability evaluation includes an on-line eligibility questionnaire, laboratory assessments, electrocardiogram (ECG), review of medical and psychiatric records, and comprehensive consultation by the investigator. Results identify patients who should be excluded because of active medical or acute psychiatric problems that might make study participation unsafe.

During Part I and Part II, safety and tolerability evaluations are performed by the investigator, registered dietitian nutritionist and research associate during scheduled and unscheduled visits, and will include qualitative assessment, frequent weight monitoring, review of questionnaires, and monitoring during clinic visits described below.

An adverse event (AE) is defined as any untoward medical occurrence in a study participant, temporally associated with the use of the modified ketogenic diet or racemic ketamine infusion, whether or not considered related to the medication. An adverse event can therefore be any unfavorable and unintended sign, symptom, significant weight loss (2 lbs or 0.9 kg on 2 consecutive days) or disease (new or exacerbated), temporarily associated with the use of either the modified ketogenic diet, or racemic ketamine infusion(s), or the sequenced 2-part procedure. A serious adverse event (SAE) will be defined as an AE that meets any of the following criteria:
Life-threatening
Requires inpatient hospitalization
Results in a persistent or significant disability/incapacity
Any other adverse event that, based upon appropriate medical judgment, may jeopardize the participant's health and may require medical or surgical intervention to prevent one of the outcomes above Monitoring for AEs is conducted during scheduled and unscheduled visits, if clinical concerns arise. Safety and tolerability aspects of the data are tabulated. Assessments includes the frequency and severity of treatment-emergent adverse events (TEAEs) and SAEs, clinical evaluations including vital sign measurements during clinic visits, and body weight. All safety assessments are reviewed by the investigator.

When an AE/SAE occurs, it is the responsibility of the investigator to immediately notify the PCP, order lab tests and ECG if required, and coordinate further investigation and follow-up with the PCP. The investigator reviews all documentation (e.g., ER or hospital progress notes, treating clinician progress notes, laboratory and diagnostic reports) relative to the event. The investigator records all relevant information regarding an AE/SAE and attempts to establish a diagnosis of the event based on signs, symptoms, and/or other clinical information.

If a participant experiences significant weight loss as an AE (≥2 lbs (0.9 kg)) on 2 consecutive days), the investigator discusses the issue with the participant, notifies the PCP, and decides whether the participant is to be given an opportunity to regain the weight in a very short time frame in order to remain in the study, or is to be withdrawn from the study.

All safety data are reported to the TRB annually, or in the case of any major safety concern or question, immediately.

Participant Withdrawal or Termination

If a participant is withdrawn at any time after acceptance, the investigator makes every effort to meet with the participant and complete a final study visit as soon as possible, ideally within 1 week of discontinuation of the other scheduled study procedures.

Participants may withdraw from the study at any time without stating a reason and without prejudice to further treatment. The investigator may withdraw a participant from the study and discontinue study treatment and assessments at any time. Early discontinuation of any participant who has given informed consent to participate is recorded including the reason for discontinuation. The primary reason for a participant withdrawing prematurely is selected from one of the following standard categories of early discontinuation:

Failure to Meet Enrollment Criteria
Adverse Event: Clinical events occurred or are reported that in the medical judgment of the investigator are grounds for discontinuation in the best interests of the participant.
Withdrawal of Consent: The participant desired to withdraw from further participation in the study. The participant is not obliged to provide any reason for withdrawal of consent, but where a reason is given, this will be recorded.
Protocol Violation: The participant failed to adhere to the protocol requirements, at the investigator's discretion.
Lost to Follow-Up: The participant stopped coming for visits and study personnel were unable to contact the participant or support partner. Every effort will be made to re-contact the participant prior to declaring a participant as lost to follow-up, which must be at least 3 documented attempts. The third must be in writing and confirmed to have been received (e.g., registered mail).

Other: The participant was withdrawn for a reason other than those listed above, such as termination of the clinical trial.

In addition, participants may withdraw during Part I and before beginning ketamine infusions in Part II because they are satisfied with the response of their SE-AN symptoms to the adoption of the modified ketogenic diet.

Handling of Participant Withdrawal or Termination

If a participant is withdrawn from active study during screening, they are returned to their PCP and standard care will be recommended.

If a participant is withdrawn from active study during either Part I or Part II, they are also returned to their PCP and standard care is recommended. However, in this case, a final study visit is requested. The participant may be requested to have clinical and laboratory safety assessments performed.

The final study visit documents the reason for withdrawal or termination. In the event that the reason for withdrawal is satisfaction with the response to the modified ketogenic diet alone, the investigator offers the participant the opportunity for follow-up for 12 months at the same schedule that would have been followed had the participant completed Part II.

Premature Termination of Participation Due to Adverse Event

The following criteria are used to identify adverse treatment events which will indicate the need to halt the participation of a participant:

Withdrawal of consent

Investigator or any regulatory authority, include IRB, believe withdrawal is necessary for the participant's health, well-being, or best interests Any serious related adverse event (SAE) results in halting the study for the individual All safety data are reported to the IRB as required. Any major safety concern or question are reported to the IRB immediately.

Premature Halting or Suspension of Study

The study is halted if one participant experiences a stopping condition.

A stopping condition means a single SAE so substantial that, in the judgment of the investigator, or the IRB, the study should be halted. Any stopping condition is reported to the IRB immediately, and the study is halted pending review by the IRB, and until the decision by regulatory authorities to resume, suspend or close the study has been made.

Exceptions for this criterion for the stopping condition are participants who withdraw or are withdrawn for reasons not directly related to or intrinsic to the study.

"Halting" of the study means that no further screening of new participants and no new initiation of Part I or Part II for any participant will occur until the safety issue has been investigated and resolved. Enrolled participants who have no new symptoms or AEs will ordinarily be allowed to continue in the study without interruption while the safety issue is being investigated, unless it is the contemporaneous judgment of the investigator or the subsequent judgment of the IRB that it is unsafe to do so, in which case all study interventions will be suspended.

All safety data are reported to the IRB as required. Any major safety concern or question are reported to the IRB immediately.

REFERENCES

1. Bachner-Melman, R., et al., Measuring recovery from an eating disorder; the psychometric properties and validity of the Eating Disorders Recovery Questionnaire, currently under review in Eating and Weight Disorders, June, 2020.
2. Barboriak, J. J., et al., Effect of diet on self-starvation in the rat, J. Nut., 1972, 102(11):1543-1546.
3. Brown, A. J., et al., A high fat diet prevents and reverses the development of activity-based anorexia in rats, Int. J. Eat. Disord., 2008, 41(5):383-389.
4. Calabrese, L., Titrated serial ketamine infusions stop outpatient suicidality and avert ER visits and hospitalizations, Int. J. Psychiatr. Res., 2019, 2(6):1-12.
5. Carpenter, W. T., The schizophrenia ketamine challenge study debate, Biol. Psychiatry, 1999, 46(8):1081-1091.
6. Chen, Y. W., et al., Single injection of ketamine during mid-adolescence promotes long-lasting resilience to activity based anorexia of female mice by increasing food intake and attenuating hyperactivity as well as anxiety like behavior, Int. J. Eat. Disord., 2018, 51:1020-1025.
7. Fairburn, C. G., et al., Assessment of eating disorders: Interview or self-report questionnaire? Int. J. Eat. Disord., 1994, 16(4):363-370.
8. Feifel, D., et al., Safety of repeated administration of parenteral ketamine for depression, Pharmaceuticals, 2020, 13(7):151.
9. Froreich, F. V., et al., Blind versus open weighing from an eating disorder patient perspective, J. Eating Disorders, 2020, 8:39.
10. Goldberg, M. D., et al., Multi-day low dose ketamine infusion for the treatment of complex regional pain syndrome, Pain Physician, 2005, 8(2):175-179.
11. Guisinger, S., Adapted to flee famine: Adding an evolutionary perspective on anorexia nervosa, Psychological Review, 2003, 110(4):745-761.
12. Hartman, A. L., et al., The new ketone alphabet soup: BHB, HCA, and HDAC, Epilepsy Curr., 2014, 14(6):355-357.
13. Hay, P. J., et al., Treatment for severe and enduring anorexia nervosa: A review, Australian and New Zealand Journal of Psychiatry, 2012, 46(12):1136-1144.
14. Kossoff, E. H., et al., Optimal clinical management of children receiving dietary therapies for epilepsy: Updated recommendations of the International Ketogenic Diet Study Group, Epilepsia Open., 2018, 3(2):175-192.
15. Kroenke, K., et al., The patient health questionnaire somatic, anxiety and depressive symptom scales: A systematic review, Gen. Hosp. Psychiatry, 2010, 32(4):345-359.
16. Lahti, A. C., et al., Long-term outcome of patients who receive ketamine during research, Biol. Psychiatry, 2001, 49(10):869-875.
17. Mills, I. H., et al., Treatment of compulsive behaviour in eating disorders with intermittent ketamine infusions, QJM: An International Journal of Medicine, 1998, 91(7): 493-503.
18. Mond, J. M., et al., Eating disorder examination questionnaire (EDE-Q): Norms for young adult women, Behaviour Research and Therapy, 2006, 44(1):53-62.
19. Morgan, C. J. A., et al., Acute effects of ketamine on memory symptoms and psychotic symptoms in healthy volunteers, Neuropsychopharmacology, 2004, 29(1):208-218.
20. Schebendach, J. D., et al., Fat preference and fat intake in individuals with and without anorexia nervosa, Appetite, 2019, 139:35-41.
21. Scolnick, B., et al., Remission from chronic anorexia nervosa with ketogenic diet and ketamine: Case report, Frontiers in Psychiatry, 2020, 11:763.

22. Thompson, F. E., et al., The National Cancer Institute's dietary assessment primer: A resource for diet research, J. Acad. Nutr. Diet., 2015, 115(12):1986-1995.
23. Touyz, S., et al., Severe and enduring anorexia nervosa (SE-AN): In search of a new paradigm, J. Eat. Disord., 2015, 3:26.
24. Broomfield, C., et al., Labeling and defining severe and enduring anorexia nervosa: A systematic review and critical analysis, Int. J. Eat Disord., 2017, 50(6):611-623.

We claim:

1. A method of treating anorexia nervosa and related clinical syndromes in a subject in need thereof, said method comprising:
   a) placing the subject on a ketogenic diet and maintaining the subject on the ketogenic diet for a period of time sufficient to cause a detectable increase in ketone levels above levels associated without a ketogenic diet; and
   b) administering an effective amount of a pharmaceutical composition comprising ketamine or a pharmaceutically acceptable salt thereof, to the subject,
   wherein combination of the ketogenic diet and administration of the pharmaceutical composition comprising ketamine or the pharmaceutically acceptable salt thereof, is effective to treat said anorexia nervosa in the subject.

2. The method according to claim 1, wherein the subject on the ketogenic diet has a blood ketone level of from about 0.3 mmol/L to about 3.0 mmol/L of β-hydroxybutyrate.

3. The method according to claim 1, wherein the ketogenic diet restricts meals taken by the subject to comprise fats and the combination of proteins and carbohydrates in a ratio from about 4:1, to about 1:1 by weight.

4. The method according to claim 1, wherein the period of time in which the subject is maintained on the ketogenic diet is at least about 3 months.

5. The method according to claim 1, wherein ketamine or the pharmaceutically acceptable salt thereof is in a form of a racemic mixture of esketamine and arketamine.

6. The method according to claim 1, wherein the effective amount of the pharmaceutical composition administered to the subject is from about 0.3 mg/kg to about 1.5 mg/kg body weight.

7. The method according to claim 1, wherein the subject is administered with 3 to 6 doses of the pharmaceutical composition for a period between 3 to 6 weeks.

8. The method according to claim 1, wherein the subject is administered with an initial dose of the pharmaceutical composition comprising a first amount of ketamine or the pharmaceutically acceptable salt thereof, followed by one or more doses of the pharmaceutical composition comprising a second amount of ketamine or the pharmaceutically acceptable salt thereof, wherein the second amount of ketamine is greater than the first amount of ketamine.

9. The method according to claim 1, wherein the subject is administered with an initial dose of the pharmaceutical composition comprising a first amount of ketamine or the pharmaceutically acceptable salt thereof, followed by one or more doses of the pharmaceutical composition comprising a second amount of ketamine or the pharmaceutically acceptable salt thereof, wherein the second amount of ketamine is less than the first amount of ketamine.

10. A method of treating bulimia in a subject in need thereof, said method comprising:
    a) placing the subject on a ketogenic diet and maintaining the subject on the ketogenic diet for a period of time sufficient to cause a detectable increase in ketone levels above levels associated without a ketogenic diet; and
    b) administering an effective amount of a pharmaceutical composition comprising ketamine or a pharmaceutically acceptable salt thereof to the subject,
    wherein combination of administration of the pharmaceutical composition comprising ketamine or the pharmaceutically acceptable salt thereof, and the ketogenic diet is effective to treat said bulimia in the subject.

11. The method according to claim 10, wherein the ketogenic diet restricts meals taken by the subject to comprise fats and the combination of proteins and carbohydrates in a ratio from about 4:1, to about 1:1 by weight.

12. The method according to claim 10, wherein the ketogenic diet results in a blood ketone level of from about 0.3 mmol/L to about 3.0 mmol/L of β-hydroxybutyrate in the subject.

13. The method according to claim 10, wherein the pharmaceutical composition comprises ketamine or the pharmaceutically acceptable salt thereof in a form of a racemic mixture of esketamine and arketamine.

14. The method according to claim 10, wherein the effective amount of the pharmaceutical composition administered to the subject is from about 0.3 mg/kg to about 1.5 mg/kg body weight.

15. The method according to claim 1, wherein the ketamine is esketamine or the pharmaceutically acceptable salt thereof.

16. The method according to claim 10, wherein the ketamine is esketamine or the pharmaceutically acceptable salt thereof.

17. The method according to claim 1, wherein the patient has a BMI less than 17 kg/m².

18. The method according to claim 1, wherein the effective amount of the pharmaceutical composition administered to the subject is the amount required for the patient to begin to exhibit dissociative symptoms.

19. The method according to claim 10, wherein the effective amount of the pharmaceutical composition administered to the subject is the amount required for the patient to begin to exhibit dissociative symptoms.

20. The method according to claim 1, wherein the ketogenic diet is a diet with 60% to 82% of total daily calories from fat, 5% to 15% of total daily calories from carbohydrates, and 12% to 30% of total daily calories from protein.

21. The method according to claim 10, wherein the ketogenic diet is a diet with 60% to 82% of total daily calories from fat, 5% to 15% of total daily calories from carbohydrates, and 12% to 30% of total daily calories from protein.

* * * * *